US005596409A

United States Patent [19]

Marcus et al.

[11] Patent Number: 5,596,409
[45] Date of Patent: Jan. 21, 1997

[54] ASSOCIATED DUAL INTERFEROMETRIC MEASUREMENT METHOD FOR DETERMINING A PHYSICAL PROPERTY OF AN OBJECT

[75] Inventors: Michael A. Marcus, Honeoye Falls; Stanley Gross, Rochester; David C. Wideman, Fairport, all of N.Y.

[73] Assignee: Eastman Kodak Company, Rochester, N.Y.

[21] Appl. No.: 408,770

[22] Filed: Mar. 22, 1995

[51] Int. Cl.⁶ ......................................... G01B 9/02
[52] U.S. Cl. ............................. 356/357; 356/346
[58] Field of Search .................... 356/345, 346, 356/357, 359, 360, 361

[56] References Cited

U.S. PATENT DOCUMENTS

| | | | |
|---|---|---|---|
| 3,286,582 | 11/1966 | Mertz . | |
| 3,319,515 | 5/1967 | Flournoy . | |
| 3,790,284 | 2/1974 | Baldwin . | |
| 4,138,727 | 2/1979 | Mantz | 356/346 |
| 4,165,182 | 8/1979 | Vilkomerson | 356/349 |
| 4,367,951 | 1/1983 | Hammon | 356/357 |
| 4,443,106 | 4/1984 | Yasuda et al. | 356/357 |
| 4,631,498 | 12/1986 | Cutler . | |
| 4,639,138 | 1/1987 | Martin et al. | 356/350 |
| 4,645,349 | 2/1987 | Tabata . | |
| 4,681,447 | 7/1987 | Davidson | 356/351 |
| 4,710,001 | 12/1987 | Lacey | 350/346 |
| 4,711,574 | 12/1987 | Baldwin | 356/349 |
| 4,765,741 | 8/1988 | Detro et al. | 356/358 |
| 4,883,357 | 11/1989 | Zanoni et al. | 356/349 |
| 4,930,894 | 6/1990 | Baldwin | 356/351 |
| 4,958,930 | 9/1990 | Robertson, Jr. | 356/357 |
| 4,983,823 | 1/1991 | Isobe | 250/225 |
| 4,984,894 | 1/1991 | Kondo | 356/382 |
| 5,042,949 | 8/1991 | Greenberg et al. | 356/345 |
| 5,110,211 | 5/1992 | Niki et al. | 356/346 |
| 5,202,745 | 4/1993 | Sorin et al. | 356/73.1 |
| 5,229,832 | 7/1993 | Gaynor | 356/360 |
| 5,268,738 | 12/1993 | Baney et al. | 356/345 |
| 5,268,741 | 12/1993 | Chou et al. | 356/351 |
| 5,285,261 | 2/1994 | Dumoulin | 356/432 |
| 5,291,267 | 3/1994 | Sorin et al. | 356/345 |
| 5,331,400 | 7/1994 | Wilkening et al. | 356/349 |

OTHER PUBLICATIONS

Optics Letters/vol. 12, No. 3/Mar. 1987/pp. 158–160, Optical Coherence–Domain Reflectometry: A New Optical Evaluation Technique, R. C. Youngquist, S. Carr, & D. E. N. Davies.

Applied Optics/vol. 26, No. 14/15 Jul. 1987, pp. 2836–2842, Guided wave reflectometry with micrometer resolution, B. L. Danielson & C. D. Whittenberg.

Journal of Lightwave Technology/vol. 9/No. 5, May 1991, pp. 623–628, Polarization–Independent Interfometric Optical–Time–Domain Reflectometer, M. Kobayashi, H. Hanafusa, K. Takada, & J. Noda.

Hewlett–Packard Journal/Feb. 1993/pp. 39–48, Design of a Precision Optical Low–Coherence Reflectometer, D. H. Booster, H. Chou, M. Hart, S. Mifsud, & R. Rawson.

Hewlett–Packard Journal/Feb. 1993/pp. 52–59, High–Resolution and High–Sensitivity Optical Reflection Measurements Using White–Light Interferometry, H. Chou & W. Sorin.

Applied Optics/vol. 11, No. 9/Sep. 1972/pp. 1905–1906, Optic in DuPont, P. A. Flournoy.

(List continued on next page.)

*Primary Examiner*—Samuel A. Turner
*Assistant Examiner*—Amanda Merlino
*Attorney, Agent, or Firm*—Susan L. Parulski

[57] ABSTRACT

The present invention relates to an apparatus and method for measuring physical properties of an object, such as thickness, group index of refraction, and distance to a surface. The apparatus includes a non-coherent light interferometer (53) and a coherent light interferometer (55) in association so as to share a variable optical path delay element (54). Thickness measurements can be made, for example, of solids, liquids, liquids moving along a horizontal plane, or liquids flowing down a plane. Thickness measurements of multiple layers can be made.

19 Claims, 21 Drawing Sheets

OTHER PUBLICATIONS

Applied Optics/vol. 11, No. 9/pp. 1907–1915, White–Light Interferometric Thickness Gauge, P. A. Flournoy, R. W. McClure, & G. Wyntjes.

Applied Optics/vol. 30 No. 21/Jul. 20, 1991/pp. 2975–2979, Absolute Optic Ranging Low Coherence Interferometry, B. L. Danielson & C. Y. Boisrobert.

ASSOCIATED DUAL INTERFEROMETRIC MEASUREMENT METHOD FOR DETERMINING A PHYSICAL PROPERTY OF AN OBJECT

CROSS REFERENCE TO RELATED APPLICATIONS

This application is related to the application titled, "ASSOCIATED DUAL INTERFEROMETRIC MEASUREMENT APPARATUS", by Marcus, Gross, and Wideman, filed this same date, by the same assignee.

FIELD OF THE INVENTION

The invention relates to the measurement of physical properties of an object by non-contact optical interferometry. More particularly, the invention concerns an apparatus and method for measuring physical properties such as thickness, group index of refraction, and distance to a surface.

BACKGROUND OF THE INVENTION

In web and coating manufacturing operations, there is a need for an apparatus for accurate, on-line measurements of web and coating layer thickness. Such an apparatus should have a fast response time and a high degree of lateral resolution; and should be portable, light weight, compact, and easy to set up. Further, there is a need for such an apparatus which can be readily installed in high and low temperature environments, in the presence of solvents, high air flow, and various levels of relative humidity. In addition, there is a need for such an apparatus which is self-calibrating or able to remain in calibration for extended periods of time so that the apparatus can be installed on a production machine without the need for re-calibration.

Driving forces for this invention are the needs to achieve improved manufacturing process understanding and perform on-line manufacturing process capability assessments in a minimum amount of time. A high level of portability is needed to enable short turn-around time during troubleshooting activities for production quality problems.

The invention relates to the measurement of physical properties of an object by optical interferometry. Accordingly, a brief background discussion is presented regarding non-coherent and coherent light interferometers.

The coherence length of a light source is the distance over which the phase relationships of a light beam originating from the light source remain correlated. For a coherent light source with a long-coherence length, such as a helium-neon laser, this distance can be many kilometers. In contrast, for a non-coherent broadband white-light source such as sunlight, this distance is only a few micrometers (microns). For example, typical broadband light emitting diodes (LED) have coherence lengths on the order of 8–15 μm.

FIG. 1 shows a block diagram of a prior art fiberoptic embodiment of a non-coherent light interferometer 10 in a Michelson configuration. Non-coherent interferometer 10 has a non-coherent light source 14 emitting a non-coherent light signal. The non-coherent light signal from non-coherent light source 14 is coupled into a single-mode optical fiber 16. Single-mode optical fiber 16 comprises one arm of a 2×2 optical coupler 18 used as a splitting means. Optical coupler 18 divides the non-coherent light signal from non-coherent light source 14 traveling along single-mode optical fiber 16 into first and second light signals, of substantially equal intensity, traveling along single-mode optical fibers 20 and 22, respectively. The first light signal traveling along single-mode optical fiber 20 is incident on an applying and collecting means 24. The first light signal is coupled to an object 25 through applying and collecting means 24. A portion of the first light signal is then reflected back from object 25 into single-mode optical fiber 20 through applying and collecting means 24. The second light signal, traveling along single-mode optical fiber 22 is incident on a collimating applying and collecting means 26. This second light signal is collimated by collimating applying and collecting means 26 and the collimated second light signal is directed towards an optical element 28, such as a retroreflector, mirror, or a combination of the two. A portion of the collimated light originating from the second light signal is reflected back from optical element 28 and is coupled back into single-mode optical fiber 22 by collimating applying and collecting means 26. Optical element 28 is mounted onto an actuation means 30, such as a motorized translation stage, a driven screw mechanism, or a voice-coil actuator (hereinafter called motor 30), which provides for precision movement of optical element 28 in a direction shown by an arrow A. The speed of motor 30 is controlled accurately so that when optical element 28 is reciprocated, the velocity of optical element 28 is a constant during the time intervals at which measurements are performed (i.e., a measurement cycle).

In operation, the first and second light signals traveling along single-mode optical fibers 20 and 22, respectively, are reflected back to optical coupler 18 where they recombine to form a recombined light signal, and a portion of the recombined light signal is directed into a photodetector 32 by a single-mode optical fiber 34. Photodetector 32 is used to measure the recombined light signal strength as a function of the displacement of optical element 28.

Non-coherent light interferometer 10 includes four branches: a non-coherent light source branch, an object branch, a reference branch, and a detection branch. The light source branch comprises the path from non-coherent light source 14 to optical coupler 18. The total optical path from optical coupler 18 to object 25 and back to optical coupler 18 is defined as the optical path length of the object branch of noncoherent light interferometer 10. Similarly, the total optical path from optical coupler 18 to optical element 28 and back to optical coupler 18 is defined as the optical path length of the reference branch of non-coherent light interferometer 10. Likewise, the path from optical coupler 18 to photodetector 32 is defined as the detection branch of non-coherent light interferometer 10. The object branch and the reference branch are referred to as the interfering branches of non-coherent light interferometer 10.

During operation of non-coherent light interferometer 10, motor 30 drives optical element 28 closer and further away from collimating applying and collecting means 26. As optical element 28 is moved closer and further, the optical path length of the reference branch is varied. This scanning interrogates different depths of object 25 as optical element 28 is traversed in either direction.

Since non-coherent light source 14 has a short coherence length, constructive interference in the recombined light signal occurs only when the light signals in the object branch and reference branch of interferometer 10 are mutually coherent. Mutual coherence occurs when the object branch and reference branch are of nearly equal optical path length. The maximum magnitude of the constructive interference signal occurs when the optical path lengths of the object branch and reference branch are equal. A series of interference fringes will be observed as optical element 28 is scanned through the region of mutual coherence. The intensity of these interference fringes will vary from zero to a maximum over a few coherence lengths of the light source.

For constructive interference to occur, there also needs to be a reflected light signal coming from object 25 which is coupled back into single-mode optical fiber 20. To obtain a reflected light signal coming from object 25 at a given interrogation depth, there must be an optical interface between adjacent optical media of object 25 with differing group index of refraction. This can occur, for example, at a fiber-optic connector-to-air interface, the air-to-object front surface interface, and the object second surface-adjacent-media interface (if one exists). Constructive interference will thus be observed at positions of optical element 28 wherein the optical path length of the reference branch is equal to the optical path length of the object branch within a few coherence lengths for each of the object's optical media interfaces of differing group index of refraction.

Referring still to FIG. 1, optical element 28 is mounted for precision movement by motor 30 in a direction shown by the arrow A. Constant-velocity control of motor 30 is utilized to obtain accurate measurements. Use of constant velocity enables calculation of motor distance traveled from measured time intervals. Constant velocity is typically obtained by means of an active servo control loop which generates a velocity versus time graph for optical element 28 (and accordingly for motor 30), such as that shown in FIG. 2. The acceleration and deceleration phases at each end of the measurement cycle are variable-velocity zones where accurate measurements cannot be made. The acceleration phase occurs between points a and b, the constant-velocity phase is shown between points b and c, and the deceleration phase occurs between points c and d. In practice, it is difficult to minimize velocity variations between points b and c to the desired degree. This difficulty limits the precision of the instrument. Since there is also the possibility for hysteresis and backlash accumulation, measurements are usually made during travel in one direction only. A typical measurement cycle would be as follows. A measurement is performed when optical element 28 (as illustrated in FIG. 1) is moving from left to right during part of the constant-velocity phase b to c. In practice, a home reference position e (as shown in FIG. 2) would also be detected in order to ensure that the constant-velocity phase b to c has been reached. FIG. 2 shows the time at which the motor crosses the home reference position e, labeled as point e. This location of point e would vary from scan to scan due to hysteresis and backlash of motor 30. The measurement cycle would be started when the motor passes home reference position e while traveling from left to right.

FIG. 3 shows a block diagram of a typical Michelson based coherent light interferometer 40. Interferometer 40 includes a coherent light source 42, such as a laser, emitting a collimated coherent light signal. The coherent light signal emitted from coherent light source 42 is split at point B of a splitting means 44, such as a beam splitter, into first and second light signals of approximately equal intensity. The first light signal is incident onto a stationarily mounted retroreflector 46. The second light signal is incident onto an optical element 48, such as a retroreflector (hereinafter referred to as retroreflector 48), mounted for precision movement by motor 30 in a direction shown by arrow A. The first and second light signals are retro-reflected back to beam splitter 44 where they recombine at point C and interfere with each other. This recombined, interference signal is detected by a photodetector 50.

Coherent light interferometer 40 includes four branches: a coherent light source branch, a stationary branch, a reference branch, and a detection branch. The total optical path from point B of beam splitter 44 to retroreflector 46 and back to point C of beam splitter 44, is defined as the optical path length of the stationary branch of coherent light interferometer 40. Similarly, the total optical path from point B of beam splitter 44 to retroreflector 48 and back to point C of beam splitter 44, is defined as the optical path length of the reference branch of coherent light interferometer 40. The coherent light source branch and detection branch of the coherent light interferometer follow the definitions for the light source branch and detection branch, respectively, of non-coherent light interferometer 10.

Since coherent light source 42 has a long coherence length, the stationary branch and the reference branch of coherent light interferometer 40 need not have equal optical path lengths in order for an interference signal to be detected at photodetector 50. Since this is the case, interference fringes of equal amplitude will be observed over the entire range of motion of retroreflector 48.

The configuration shown in FIG. 3 can be used for a bulk non-coherent light interferometer by changing the coherent light source to a non-coherent light source, and making the path lengths of the stationary branch and reference branch equal to within a few coherence lengths of the non-coherent light source. When the stationary retroreflector, i.e. retroreflector 46, of FIG. 3 is replaced with object 25 (as shown in FIG. 1) and the path lengths of the stationary and reference branches are nearly equal, the configuration then becomes functionally equivalent to the fiber-optic implementation of the non-coherent light interferometer 10, as shown in FIG. 1.

Non-coherent light interferometers have been demonstrated to generate an optical fringe pattern that can be utilized to determine a predetermined physical property, such as thickness, of a traveling web. For example, U.S. Pat. No. 3,319,515 (Flournoy) relates to the determination of a physical property of a substance on the basis of interferometric optical phase discrimination. However, as described in U.S. Pat. No. 4,958,930 (Robertson, Jr), the measurement system described by Flournoy does not provide a mechanism whereby small variations (in the range of less than one percent) in thickness of traveling webs and coatings can be accurately gauged while on-line; that is, without removing the web or coated layer from the manufacturing line. In addition, the apparatus described in Flournoy is bulky, difficult to set up, and can not be readily utilized in many spatially constrained process environments.

The measurement approach described in Flournoy has come to be known as "Optical Coherence-Domain Reflectometry" (OCDR) as exemplified by the following articles: (1) "Optical Coherence-Domain Reflectometry: a New Optical Evaluation Technique", by Robert C. Youngquist, Sally Carr, and D. E. N. Davies, Optics Letters, Vol. 12, No. 3, March 1987, pp. 158–160; (2) "Guided-wave Reflectometry with Micrometer Resolution", by B. L. Danielson and C. D. Whittenberg, Applied Optics, Vol. 26, No. 14, Jul. 15, 1987, pp. 2836–2842; (3) "Polarization-Independent Interferometric Optical-Time Domain Reflectometer", by Masaru Kobayashi, Hiroaki Hanafusa, Kazumasa Takada, and Juichi Noda, Journal of Lightwave Technology, Vol. 9, No. 5, May 1991, pages 623–628; (4) "Design of a Precision Optical Low-Coherence Reflectometer", by D. H. Booster, H. Chou, M. G. Hart, S. J. Mifsud, and R. F. Rawson, Hewlett-Packard Journal, Vol. 44, No. 1, February 1993, pages 39–43; and (5) "High-Resolution and High-Sensitivity Optical Reflection Measurements Using White-Light Interferometry", by H. Chou and W. V. Sorin, Hewlett-Packard Journal, Vol. 44, No. 1, February 1993, pages 52–59. U.S. Pat. No. 5,202,745 (Sorin) also describes a measurement system based on the OCDR technique. Each article describes a reference mirror in one arm of a Michelson interferometer which is scanned at a constant velocity during the course of measurement. Measurement resolution on the order of a few microns has been reported. The ultimate measurement resolution attainable by this class of instruments is dependent on how precisely velocity variations can be minimized while changing the path length of the reference arm of the interferometer. The ultimate measurement resolution is also dependent on the methods used to process photodetector 32 data.

The above identified references have achieved certain degrees of success in their particular applications. However, a need has continued to exist for a high precision, compact, portable and robust apparatus for determining physical properties of an object, for example, during high-speed manufacturing of running webs and/or coatings. More specifically, there is a need for an on-line apparatus capable of high-speed thickness gauging of liquid layers and web material.

SUMMARY OF THE INVENTION

An object of the invention is to eliminate the need for constant velocity control in apparatus based on non-coherent light interferometry.

Another object of the invention is to eliminate the need for a home motor reference position in such an apparatus.

Still another object of the invention is to allow dual-direction measurement capability.

A further object of the invention is to eliminate the need for calibration of such an apparatus while installed in a manufacturing site for extended periods of time.

Still a further object of the invention is to provide an apparatus and method for determining physical properties of an object.

Yet another object of the invention is to provide an apparatus and method for measuring thickness of an object; for example, the thickness of a liquid layer, a free-falling liquid layer, a liquid layer running down a stationary inclined plane, or a liquid layer which is coated onto a moving support.

Yet a further object of the invention is to provide an apparatus and method for measuring thickness uniformity of stationary and moving webs, and stationary and moving sheet materials during their manufacture.

Another further object of the invention is to provide an apparatus and method for measuring thicknesses of coated layers on a stationary or moving substrate.

Yet a further object of the invention is to provide an apparatus and method for simultaneous measurement of liquid thickness, and group index of refraction of a liquid.

Still a further object of the invention is to precisely measure the distance from a probe reference surface to a surface of an object.

Still another object of the invention is to precisely measure surface profiles over extended regions of objects.

These objects are given only by way of illustrative examples; thus, other desirable objectives and advantages inherently achieved by the disclosed invention may occur or become apparent to those skilled in the art. The invention is defined by the appended claims.

According to one aspect of the invention, there is provided an apparatus for determining a physical property of an object. The apparatus includes a first and second interferometer. The first interferometer has a coherent light source and is adapted to form a coherent light interference signal indicative of displacment, while the second interferometer has a non-coherent light source and is adapted to form a non-coherent light interference signal indicative of the physical property of the object. The first and second interferometers are in mechanical association so as to share a common variable optical path delay element. The variable optical path delay element can be displaced over a distance sufficient to determine the physical property of the object. The apparatus further includes means for measuring the coherent light interference signal as a function of the displacement of the variable optical path delay element; means for utilizing this coherent light interference signal to generate data acquisition trigger signals at constant displacement intervals of the variable optical path delay element; and means for measuring the amplitude of the non-coherent light interference signal; and means for utilizing the data acquisition trigger signals to sample the amplitude of the non-coherent light interference signal; and means for determining the physical property of the object from the sampled non-coherent light interference signal.

According to another aspect of the invention, there is provided an apparatus including a coherent light source providing a coherent light signal; first splitting means for dividing the coherent light signal into first and second light signals; first applying means for applying the first light signal to a stationary reference device, a portion of the first light signal being reflected by the stationary reference device to form a reference signal; second applying means for applying the second light signal to a variable optical path delay element; first collecting means for collecting the reference signal; a non-coherent light source providing a non-coherent light signal; second splitting means for dividing the non-coherent light signal into third and fourth light signals; third applying means for applying a portion of the third light signal to the object, a portion of the third light signal being reflected by the object to form an object signal; second collecting means for collecting the object signal; fourth applying means for applying the fourth light signal to the variable optical path delay element, the application of the second and fourth light signals to the variable optical path delay element forming a first and second delay signal, respectively; third collecting means for collecting the first delay signal; fourth collecting means for collecting the second delay signal; actuation means in mechanical association with the variable optical path delay element, the actuation means adapted to displace the variable optical path delay element to vary the optical path length of the second light signal and the fourth light signal as a function of displacement of the variable optical path delay element, the variable optical path delay element being movable over a distance sufficient to determine the physical property of the object; first adding means for combining the first delay signal and the reference signal to form a coherent light interference signal; second adding means for combining the object signal and the second delay signal to form a non-coherent light interference signal; a first detection means for measuring the amplitude of the coherent light interference signal as a function of displacement of the variable optical path delay element; means for generating data acquisition trigger signals at constant displacement intervals of the variable optical path delay element based on the cyclic nature of the coherent light interference signal; a second detection means for measuring the amplitude of the non-coherent light interference signal; means for utilizing the data acquisition trigger signals to sample the second detection means; and means for determining the physical property of the object from the sampled second detection means.

According to a further aspect of the invention, there is provided an apparatus including a coherent light source providing a coherent light signal; first splitting means for dividing the coherent light signal into first and second light signals; first applying means for applying the first light signal to a first stationary reference device, a portion of the first light signal being reflected by the first stationary reference device to form a first reference signal; first collecting means for collecting the first reference signal; a non-coherent light source providing a non-coherent light signal; second applying means for applying a portion of the non-coherent light signal to an object, a portion of the non-coherent light signal being reflected by the object to form an object signal; second collecting means for collecting the object signal; second splitting means for dividing the object signal into third and fourth light signals; third applying means for applying the third light signal to a second stationary reference device, a portion of the third light signal being reflected by the second stationary reference device to form a second reference signal; third collecting means for collecting the second reference signal; fourth applying means for applying the second light signal to a variable optical path delay element; fifth applying means for applying the fourth light signal to the variable optical path delay element, the variable optical path delay element varying the optical path length of the second light signal and the fourth light signal, such that the application of the second and fourth light signals to the variable optical path delay element forms a first and second delay signal respectively; fourth collecting means for collecting the first delay signal; fifth collecting means for collecting the second delay signal; actuation means in mechanical association with the variable optical path delay element, the actuation means adapted to displace the variable optical path delay element to vary the optical path length of the second light signal and the fourth light signal as a function of displacement of the variable optical path delay element, the variable optical path delay element being movable over a distance sufficient to determine the physical property of the object; first adding means for combining the first delay signal and the first reference signal to form a coherent light interference signal; second adding means for combining the second delay signal and the second reference signal to form a non-coherent light signal; first detection means for measuring the amplitude of the coherent light interference signal as a function of displacement of the variable optical path delay element; second detection means for measuring the amplitude of the non-coherent light signal; means for generating data acquisition trigger signals at constant displacement intervals of the variable optical path delay element based on the cyclic nature of the coherent light interference signal; means for utilizing the data acquisition trigger signals to sample the second detection means; and means for determining the physical property of the object from the sampled second detection means.

According to an aspect of the invention, there is provided a method for determining a physical property of an object. The method includes the steps of: providing a first and second interferometer in mechanical association by means of sharing a common variable optical path delay element; displacing the variable optical path delay element over a distance sufficient to determine the physical property of the object, the first interferometer having a coherent light source and forming a coherent light interference signal; measuring the amplitude of the coherent light interference signal as a function of displacement of the variable optical path delay element; utilizing the cyclic nature of the coherent light interference signal to generate data acquisition trigger signals at constant displacement intervals of the variable optical path delay element, the second interferometer having a non-coherent light source and forming a non-coherent light interference signal indicative of the physical property of the object; measuring the amplitude of the non-coherent light interference signal; utilizing the generated data acquisition trigger signals to sample the amplitude of the non-coherent light interference signal; and determining the physical property of the object from the sampled non-coherent light interference signal.

According to another aspect of the invention, a method is provided which includes the steps of providing a coherent light source emitting a coherent light signal; dividing the coherent light signal into first and second light signals; applying the first light signal to a stationary reference device, a portion of the first light signal being reflected by the stationary reference device to form a reference signal; applying the second light signal to a variable optical path delay element to form a first delay signal; collecting the reference signal; providing a non-coherent light source emitting a non-coherent light signal; dividing the non-coherent light signal into third and fourth light signals; applying a portion of the third light signal to the object, a portion of the third light signal being reflected by the object to form an object signal; collecting the object signal; applying the fourth light signal to the variable optical path delay element to form a second delay signal; collecting the first delay signal; collecting the second delay signal; displacing the variable optical path delay element to vary the optical path length of the second light signal and the fourth light signal as a function of displacement of the variable optical path delay element, the variable optical path delay element being movable over a distance sufficient to determine the physical property of the object; combining the first delay signal and the reference signal to form a coherent light interference signal; combining the object signal and the second delay signal to form a non-coherent light interference signal; measuring the amplitude of the coherent light interference signal as a function of displacement of the variable optical path delay element; generating data acquisition trigger signals at constant displacement intervals of the variable optical path delay element based on the cyclic nature of the coherent light interference signal; measuring the amplitude of the non-coherent light interference signal; utilizing the data acquisition trigger signals to sample the second detection means; and determining the physical property of the object from the sampled second detection means.

According to yet another aspect of the invention, there is provided a method including the steps of: providing a coherent light source emitting a coherent light signal; dividing the coherent light signal into first and second light signals; applying the first light signal to a first stationary reference device, a portion of the first light signal being reflected by the first stationary reference device to form a first reference signal; collecting the first reference signal; providing a non-coherent light source emitting a non-coherent light signal indicative of the physical property of the object; applying a portion of the non-coherent light signal to the object, a portion of the non-coherent light signal being reflected by the object to form an object signal; collecting the object signal; dividing the object signal into third and fourth light signals; applying the third light signal to a second stationary reference device, a portion of the third light signal being reflected by the second stationary reference device to form a second reference signal; collecting the second reference signal; applying the second light signal to a variable optical path delay element to form a first delay signal; applying the fourth light signal to the variable optical path delay element to form a second delay signal, the variable optical path delay element varying the optical path length of the second light signal and the fourth light signal; collecting the first delay signal; collecting the second delay signal; displacing the variable optical path delay element to vary the optical path length of the second light signal and the fourth light signal as a function of displacement of the variable optical path delay element, the variable optical path delay element being movable over a distance sufficient to determine the physical property of the object; combining the first delay signal and the first reference signal to form a coherent light interference signal; combining the second delay signal and the second reference signal to form a non-coherent light signal; measuring the amplitude of the coherent light interference signal as a function of displacement of the variable optical path delay element; measuring the amplitude of the non-coherent light signal; generating data acquisition trigger signals at constant displacement interval's of the variable optical path delay element based on the cyclic nature of the coherent light interference signal; utilizing the data acquisition trigger signals to sample the second detection means; and determining the physical property of the object from the sampled second detection means.

According to still another aspect of the invention, there is provided a method including the steps of: providing a first interferometer having a coherent light source and adapted to form a coherent light interference signal; providing a second interferometer having a non-coherent light source and adapted to form a non-coherent light interference signal indicative of the physical property of the object, the first and second interferometers being in association so as to share a common variable optical path delay element; continuously monitoring the coherent light interference signal and the non-coherent light interference signal; displacing the common variable optical path delay element in a first direction; generating data acquisition trigger signals from the coherent light interference signal; sampling the non-coherent light interference signal utilizing the data acquistion trigger signals; digitizing the sampled non-coherent light interference signal; storing the digitized, sampled non-coherent light interference signal in a data array; displacing the common variable optical path delay element in a second direction, the second direction being different than the first direction; generating data acquisition trigger signals from the coherent light interference signal; sampling the non-coherent light interference signal utilizing the data acquistion trigger signals; digitizing the sampled non-coherent light interference signal; storing the digitized, sampled non-coherent light interference signal in a data array; and analyzing the stored data array to determine the physical property of the object.

According to a further aspect of the invention, there is provided a method including the steps of: providing a first interferometer having a coherent light source and adapted to form a coherent light interference signal; providing a second interferometer having a non-coherent light source and adapted to form a non-coherent light interference signal indicative of the physical property of the object, the first and second interferometers being in association so as to share a common variable optical path delay element; determining a measurement rate; determining a measurement time; continuously monitoring the coherent light interference signal and the non-coherent light interference signal; displacing the common variable optical path delay element; generating data acquisition trigger signals from the coherent light interference signal; sampling the non-coherent light interference signal utilizing the data acquistion trigger signals; digitizing the sampled non-coherent light interference signal; storing the digitized, sampled non-coherent light interference signal in a data array; and analyzing the stored data array.

The invention is based on the technique of dual optical interferometry. The invention relates to a robust, accurate, non-contact apparatus, for example, for measuring on-line web and coating layer thickness. The apparatus is highly portable, light weight, compact, and easy to set up. Further, the apparatus has a fast response time and a high degree of lateral resolution. In addition, the apparatus is capable of being readily installed in high and low temperature environments, in the presence of solvents, high air flow, and various levels of relative humidity. The apparatus provides the ability to perform on-line manufacturing process capability assessments in a minimum amount of time resulting in improved manufacturing process understanding. In practice, the apparatus can be set up within a matter of minutes at a manufacturing site once optical probe mounting brackets are installed at the selected machine location. Once properly set up and aligned in a process environment, the apparatus is capable of performing precise measurements for extended periods of time without the need for further re-adjustment. The apparatus is self-calibrated. The calibration is based upon the stability of the wavelength of the coherent light source. The high level of portability of the apparatus enables troubleshooting activities for production quality problems to proceed with a short turn-around time.

Simultaneous measurements of thickness, group index of refraction, and distance to a reference surface can be made. Thickness measurements can be made of a liquid layer of semi-transparent and photosensitive liquids in real-time without affecting the manufacturing process. The liquid can be stationary or moving, for example, free flowing, running along a horizontal plane, flowing along a curved surface, or flowing down an inclined plane. Thickness measurements can also be made on stationary or moving material (such as sheet or web material) which is semi-transparent at the wavelength of a non-coherent light source. Further, thickness measurements can be made on liquid layers coated onto a substrate. In addition, thickness measurements of each layer can be made simultaneously on webs or coated webs composed of multiple layers.

BRIEF DESCRIPTION OF THE DRAWINGS

The foregoing and other objects, features, and advantages of the invention will be apparent from the following more particular description of the preferred embodiments of the invention, as illustrated in the accompanying drawings.

DETAILED DESCRIPTION OF THE INVENTION

Figure 1:
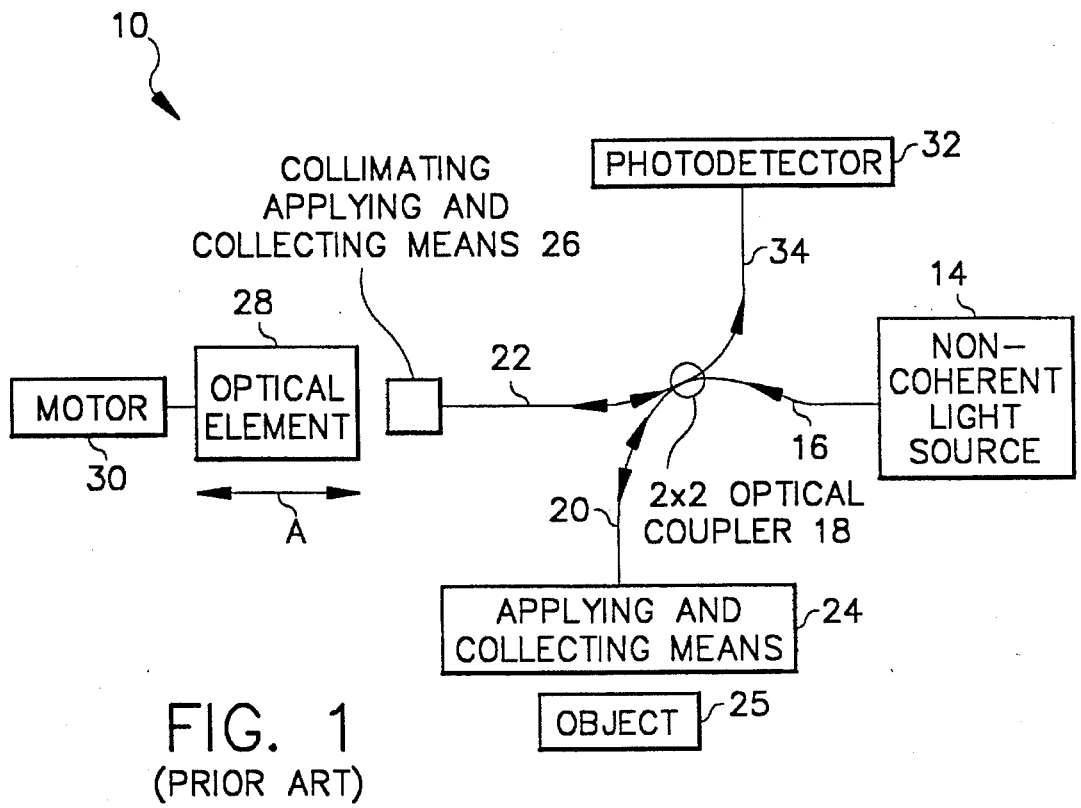
FIG. 1 shows a block diagram of an embodiment of a prior art fiber-optic based non-coherent light interferometer.

The following is a detailed description of the preferred embodiments of the invention, reference being made to the drawings in which the same reference numerals identify the same elements of structure in each of the several figures.

The invention relates to an apparatus comprising a non-coherent light interferometer and a coherent light interferometer in association so as to share a common variable optical path delay element. The invention also relates to a method for measuring physical properties of an object.

Figure 4:
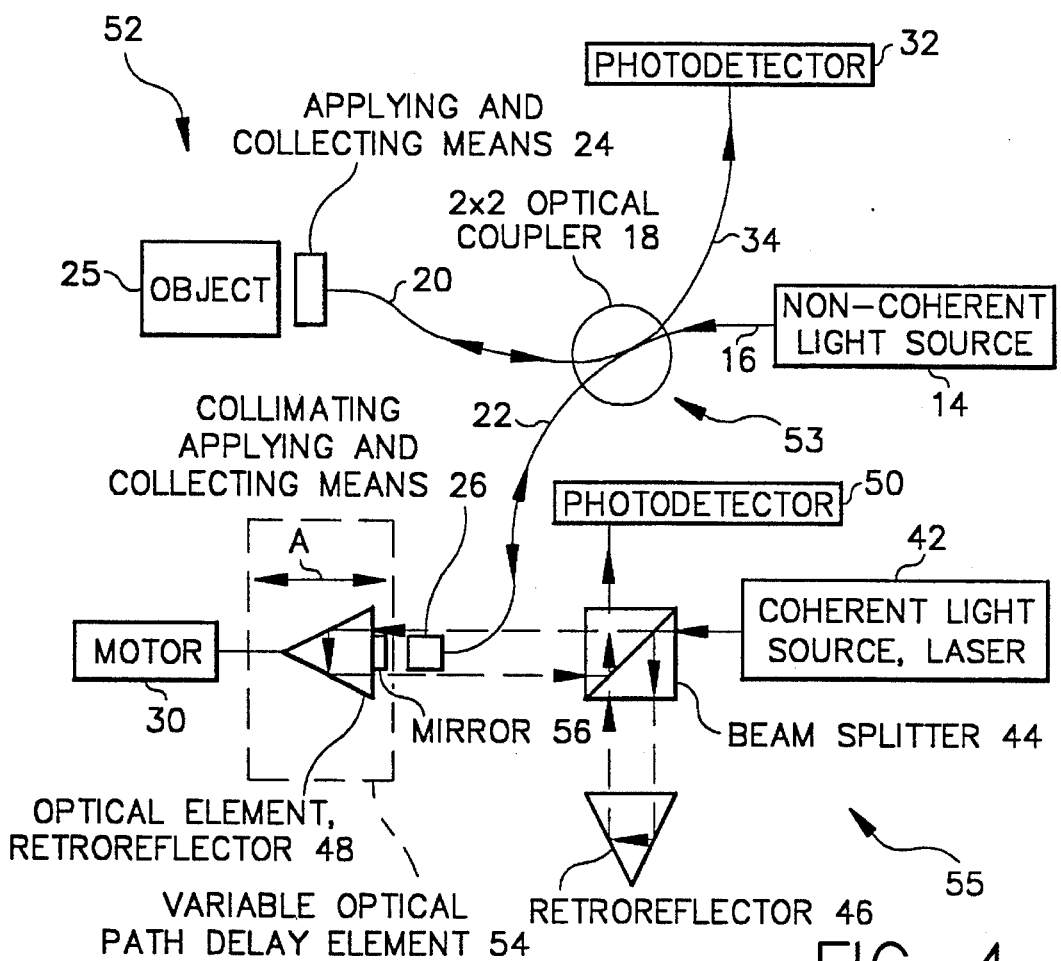
FIG. 4 shows a diagram of a first embodiment of a dual interferometer apparatus of the present invention.

FIG. 4 shows one embodiment of the present invention wherein a dual interferometer apparatus 52 comprises a non-coherent light interferometer 53 and a coherent light interferometer 55. Coherent light interferometer 55 includes coherent light source 42 which is preferably a HeNe laser or other light source having a long coherence length. (Hereinafter coherent light source 42 will be referred to as laser 42, and coherent light interferometer 55 will be referred to as laser interferometer 55.) Laser interferometer 55 also includes beam splitter 44, retroreflector 46, retroreflector 48, and photodetector 50. Likewise, non-coherent light interferometer 53 includes non-coherent light source 14, optical fiber 16, optical coupler 18, optical fibers 20, 22, applying and collecting means 24, collimating applying and collecting means 26, photodetector 32, and optical fiber 34.

In dual interferometer apparatus 52, the two interferometers 53, 55 share a common variable optical path delay element 54 in their respective reference branches. Common variable optical path delay element 54 comprises retroreflector 48, and an optical element, such as a mirror 56, mounted on a portion of retroreflector 48. Motor 30 is used to vary the optical path length of variable optical path delay element 54. The movement of motor 30 can be accomplished by an electrodynamic motor which contains a voice coil and magnet structure similar to that used in conventional cone-type loudspeakers, an appropriately compliant suspension being provided for the mirror and coil. Retroreflector 48 and mirror 56 are co-mounted for precision movement in a direction shown by arrow A under the control of motor 30. Since mirror 56 is fixedly mounted onto a portion of retroreflector 48, they both travel the same distance when variable optical path delay element 54 is moved. Accordingly, the optical path delays of laser interferometer 55 and non-coherent light interferometer 53 change simultaneously by the same magnitude as variable optical path delay element 54 (mirror 56 being mounted to retroreflector 48) is moved in the direction of travel indicated by arrow A as illustrated in FIG. 4.

Figure 2:
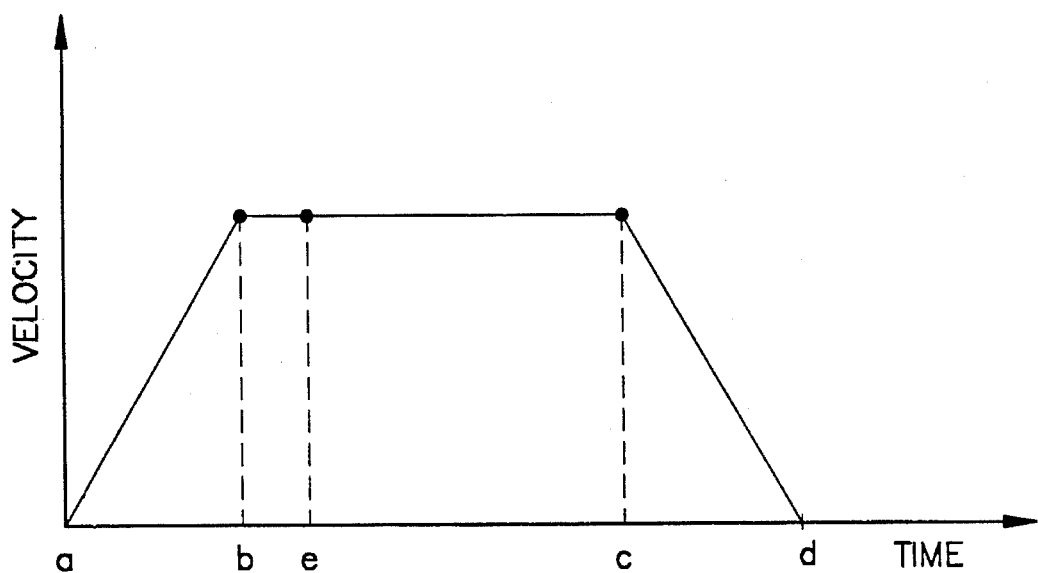
FIG. 2 shows a velocity versus time graph for an optical element illustrated in FIG. 1.
Figure 3:
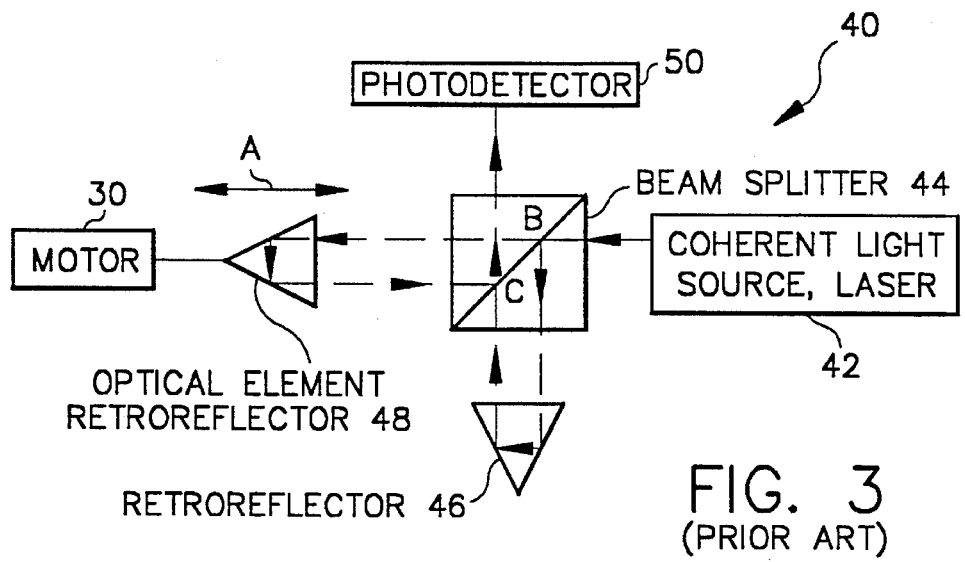
FIG. 3 shows a block diagram of a prior art bulk coherent light interferometer.

Dual interferometer apparatus 52 of FIG. 4 will hereinafter be referred to as the standard mode apparatus 52. In standard mode apparatus 52, laser interferometer 55 is incorporated for use with non-coherent light interferometer 53. The purpose of laser interferometer 55 is to accurately measure the distance which variable optical path delay element 54 moves, and to provide data acquisition trigger signals at constant distance intervals for sampling the detected signal amplitude from non-coherent light interferometer 53 at specified constant distance intervals. The non-coherent light signal amplitude is sampled at constant distance intervals and then analyzed by a computer. By actively measuring the position of variable optical path delay element 54 using laser interferometer 55, the velocity of motor 30 (and accordingly, variable optical path delay element 54) does not need to be controlled accurately. As such, a knowledge of the motor speed is not critical to the operation of the present invention. A conventional motor drive signal (such as a sine wave, saw tooth or arbitrary wave form) can be used to drive motor 30. In addition, since standard mode apparatus 52 can operate during the acceleration and deceleration regions of the motor travel (refer to the velocity versus time graph of FIG. 2), there is no need for a known external motor reference position, such as home reference position e (shown in FIG. 2) used with constant motor velocity control.

Standard mode apparatus 52 is used to determine physical properties of object 25. In standard mode apparatus 52, laser 42 emits a collimated coherent light signal which is split into first and second light signals of approximately equal intensity by beam splitter 44. The first light signal is incident onto stationarily mounted retroreflector 46. The second light signal is incident on retroreflector 48 of common variable optical path delay element 54. The first and second light signals are retro-reflected back to beam splitter 44 where they collect, recombine, and interfere with each other. This interference is detected by photodetector 50. The retro-reflected portion of the first light signal is referred to as a reference signal. The retro-reflected portion of the second light signal is called the first delay signal.

Still referring to FIG. 4, non-coherent light source 14 emits a non-coherent light signal which is coupled into single-mode optical fiber 16 comprising one arm of optical coupler 18. Light source 14 may be a light emitting diode (LED), broadband tungsten halogen lamp, an infrared glow-bar, or other non-monochromatic* light source. Preferably light source 14 is an LED, so hereinafter, light source 14 will be referred to as LED 14. As is well-known to those skilled in the art, coupling a LED to a single-mode optical fiber can be accomplished by either a LED-fiber pigtail or a lens-connector assembly (not shown). Optical coupler 18 divides the non-coherent light signal from LED 14 traveling along single-mode optical fiber 16 substantially equally into third and fourth light signals traveling along single-mode optical fibers 20 and 22, respectively. The third light signal traveling along single-mode optical fiber 20 is incident on applying and collecting means 24. Applying and collecting means 24 can be either a fiber-optic connector or a connector-lens assembly. The third light signal is directed towards object 25 by applying and collecting means 24. A portion of the third light signal is reflected back from object 25 into applying and collecting means 24 and is coupled back into single-mode optical fiber 20. This signal is referred to as the object signal. The fourth light signal, traveling along single-mode optical fiber 22, is incident on collimating applying and collecting means 26 which collimates the fourth light signal. Collimating applying and collecting means 26 can be either a fiber-optic connector or a connector-lens assembly. Collimating applying and collecting means 26 applies the fourth light signal to mirror 56 mounted on retroreflector 48 of common variable optical path delay element 54. A portion of the fourth light signal is reflected back from mirror 56 into collimating applying and collecting means 26 and is coupled back into single-mode optical fiber 22. This signal is called the second delay signal.

In operation, the third and fourth light signals traveling along single-mode optical fibers 20 and 22, respectively, are reflected back to optical coupler 18 (as the object signal and second delay signal, respectively) where they recombine and interfere with each other. A portion of the recombined object signal and second delay signal is directed into photodetector 32 by single-mode optical fiber 34. As is well-known to those skilled in the art, the optical fiber-to-photodetector coupling can be accomplished by either a fiber-optic-pigtail or a connector lens assembly (not shown). This light signal directed into photodetector 32 is referred to as a non-coherent light interferometer detector signal J.

The non-coherent light interferometer 53 of standard mode apparatus 52 includes four branches: a non-coherent light source branch, an object branch, a reference branch, and a detection branch. These branches were defined above during the discussion of non-coherent light interferometer 10. In order for constructive interference to occur at photodetector 32, the optical path lengths of the object branch and the reference branch of non-coherent light interferometer 53 must be equal to within a few coherence lengths of LED 14.

As described above, in standard mode apparatus 52, coherent light interferometer 55 and non-coherent light interferometer 53 work in association by sharing a common variable optical path delay element 54. When motor 30 moves retroreflector 48 and mirror 56 in the direction shown by arrow A, the optical path lengths of the respective reference branches of interferometers 53 and 55 vary by the same magnitude. As shown in FIG. 4, the displacement (or oscillation) of variable optical path delay element 54 is linear. The application of the second light signal and fourth light signal to retroreflector 48 and mirror 56, respectively, generates a first and second delay signal, respectively. These first and second delay signals are collected by beam splitter 44 and collimating applying and collecting means 26, respectively. Beam splitter 44 combines the first delay signal and the reference signal to form a coherent light interference signal. During operation, the distance over which common movable optical path delay element 54 travels is dependent on the application and characteristics of object 25; however, this distance must be sufficient to determine the physical property of object 25.

Object 25 can be a liquid or solid, and can be composed of single or multiple layers. Objects suitable for measurement have at least one surface which can be oriented to be near normal to the direction of propagation of a light signal which is incident on the object. For objects used in thickness measurements, the objects preferably have an optical density less than 4.0 (and more preferably, less than 2.0) at the center wavelength of a non-coherent light source and have nearly parallel (preferably within a few degrees) optical interfaces between layers. For ease of explanation, object 25 will be assumed to be a solid or liquid composed of a single layer. Accordingly, object 25 has two surfaces: a first (or front) surface, and a second (or back) surface.

Figure 5:
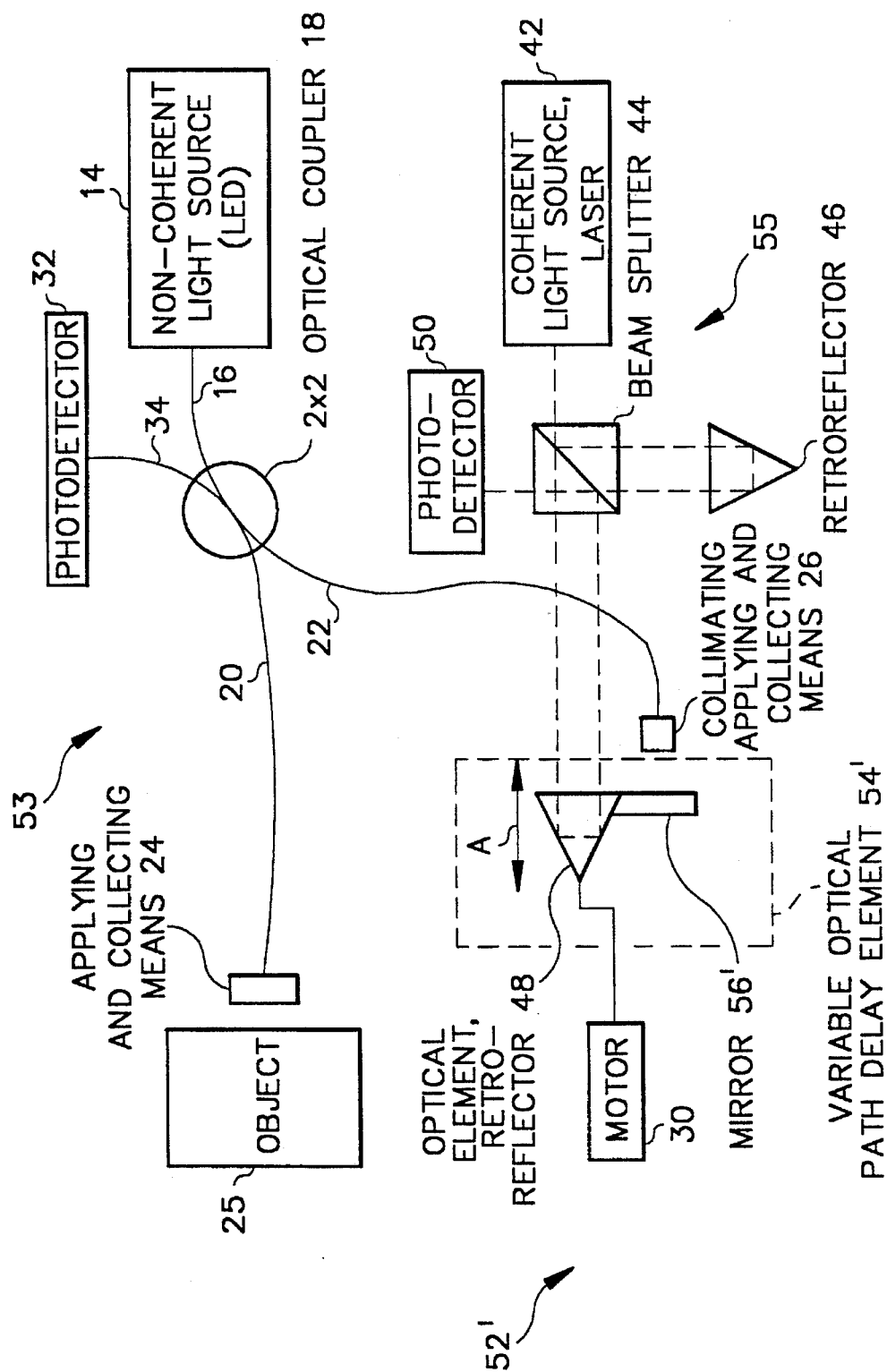
FIG. 5 shows a diagram of a second embodiment of a dual interferometer apparatus of the present invention.
Figure 6:
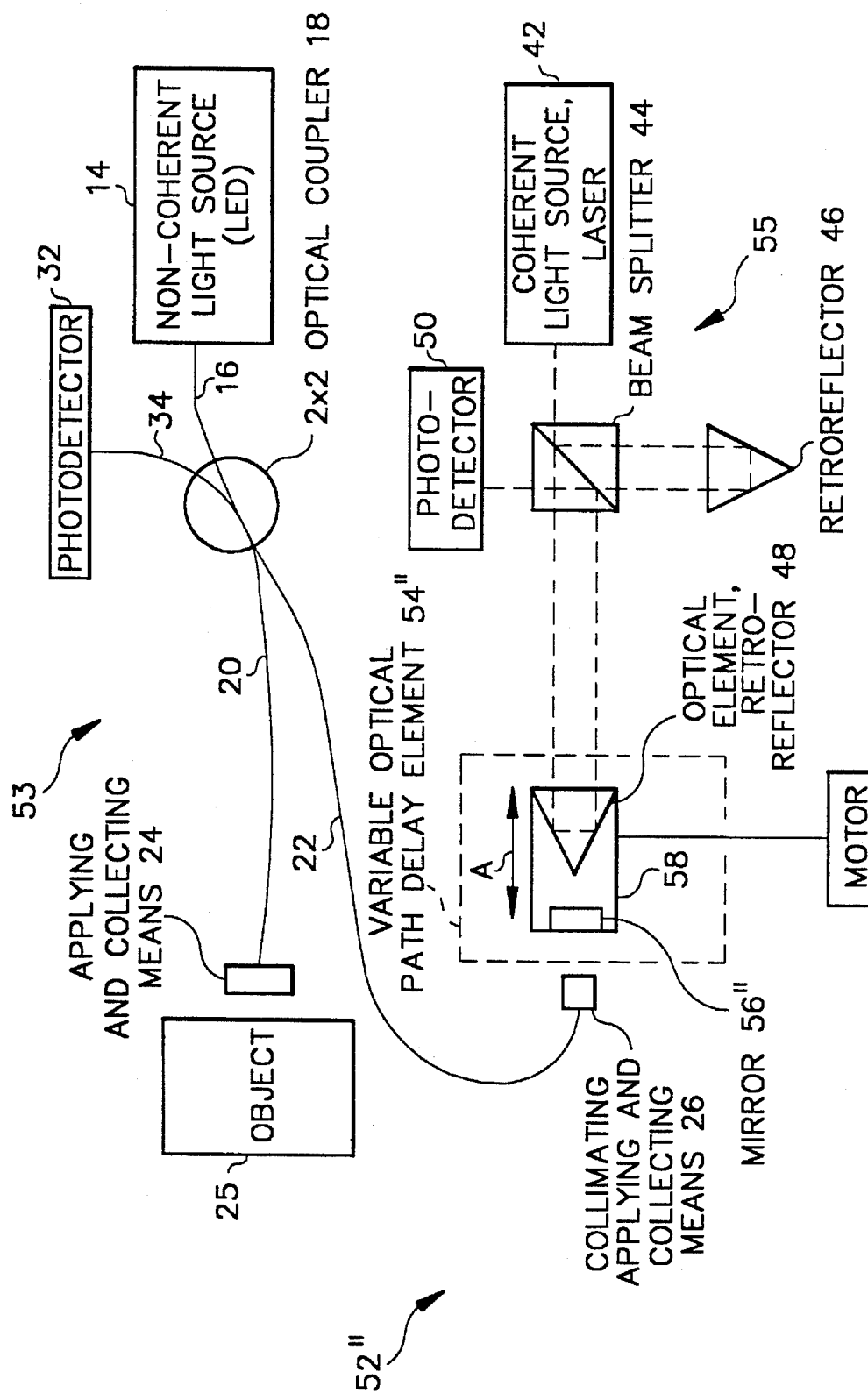
FIG. 6 shows a diagram of a third embodiment of a dual interferometer apparatus of the present invention.
Figure 7:
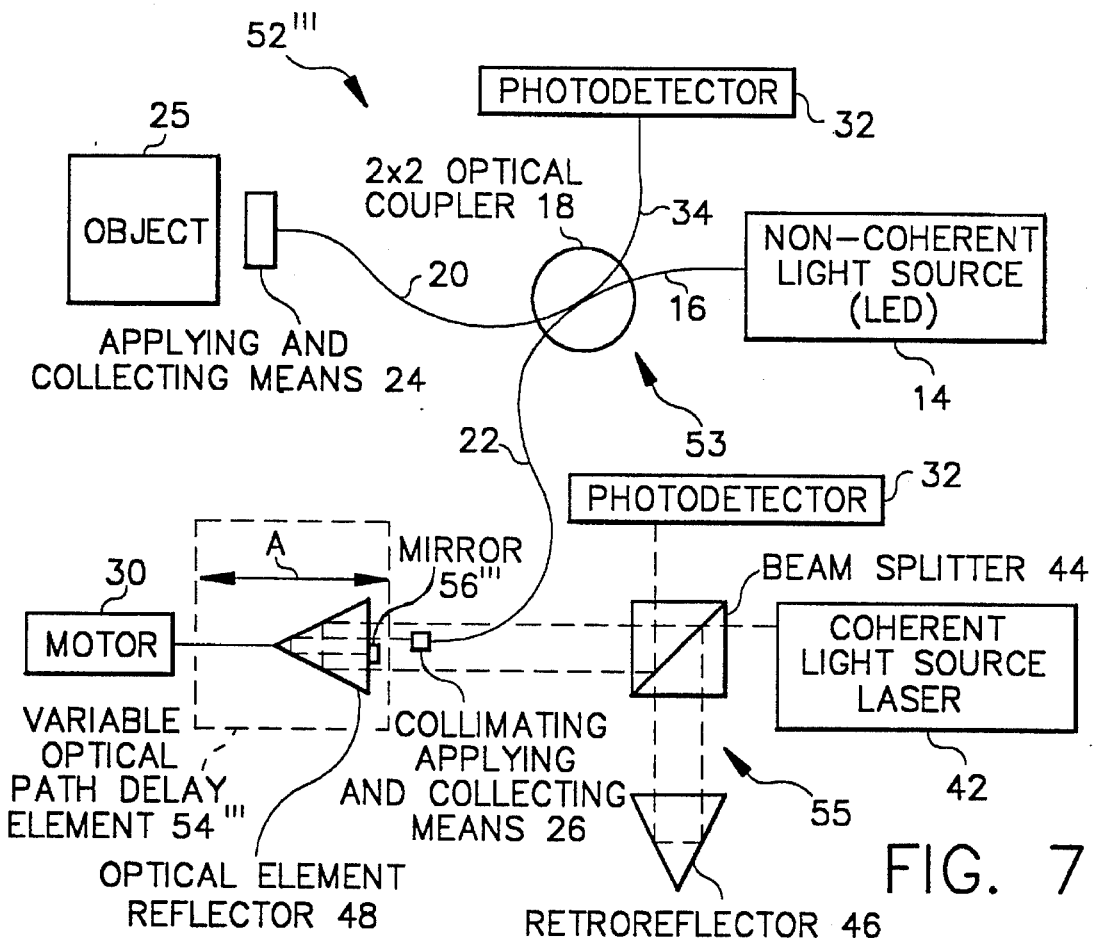
FIG. 7 shows a diagram of a fourth embodiment of a dual interferometer apparatus of the present invention.

FIG. 5, FIG. 6, and FIG. 7 show several alternative configurations of standard mode apparatus 52. FIG. 5 shows a standard mode apparatus 52' having an alternative common variable optical path delay element 54'. Common variable optical path delay element 54' includes a mirror 56' extending from retroreflector 48 such that collimating applying and collecting means 26 is not positioned along the axis formed by retroreflector 48 and beam splitter 44. Retroreflector 48 and mirror 56' must be mounted so that they are moved in unison by motor 30. This alternative positioning of mirror 56' provides an option in mounting collimating applying and collecting means 26 thereby allowing easy setup.

FIG. 6 shows an alternative standard mode apparatus 52" having an alternative common variable optical path delay element 54". In this embodiment, common variable optical path delay element 54" includes retroreflector 48, a mirror 56", and a mounting means 58. Retroreflector 48 varies the optical path length of laser interferometer 55, while mirror 56" changes the optical path length of non-coherent light interferometer 53. Retroreflector 48 and mirror 56'' are co-mounted opposing each other by means of mounting means 58. With this embodiment, when the optical path length of the reference branch of laser interferometer 55 is increased, the optical path length of the reference branch of the non-coherent light interferometer 53 is decreased by the same amount. Conversely, when the optical path length of the reference branch of laser interferometer 55 is decreased, the optical path length of the reference branch of non-coherent light interferometer 53 is increased by the same amount.

FIG. 7 shows an embodiment 52''' having alternative common variable optical path delay element 54'''. In this embodiment, the fourth light signal is coupled by optical fiber 22 to collimating applying and collecting means 26 so as to be incident on retroreflector 48, and reflected back into retroreflector 48 by a mirror 56'''. Mirror 56''' is co-mounted onto a portion of retroreflector 48 such that the reflective surface of mirror 56''' is facing retroreflector 48. This embodiment provides another mounting option for collimating applying and collecting means 26. Those skilled in the art will appreciate that further alternative mounting configurations for retroreflector 48 and mirror 56 are possible.

Measurement Principle

During operation, the cyclic nature of the coherent light interference signal from coherent light interferometer 55 is utilized to provide data acquisition trigger signals to sample the non-coherent light interference signal from non-coherent light interferometer 53 at constant distance intervals. The coherent light interference signal detected by photodetector 50 is given by the relationship:

$$I(x) = I_S + I_R + 2\sqrt{I_S I_R} \cos\left(\frac{4\pi(x-x_0)}{\lambda_c}\right) \quad (1)$$

where x is the position of retroreflector 48 relative to a reference position $x_o$;

I(x) is the photodetector signal at position x;

$I_s$ is the signal strength of the stationary branch of coherent light interferometer 55;

$I_R$ is the signal strength of the reference branch of coherent light interferometer 55; and $\lambda_c$ is the wavelength of laser 42.

Figure 8:
FIG. 8 shows a graph of a normalized coherent light signal as a function of optical delay.

FIG. 8 shows a graph of the normalized photodetector 50 signal I(x) as a function of x, the position of retroreflector 48 relative to a reference position $x_o$, for a HeNe single mode laser having a wavelength of 632,991 nm.

The photodetector 50 signal I is AC (capacitor) coupled into processing electronics which create negative going data acquisition trigger pulses on every zero crossing or some (i.e., one or more) other reproducible locations on each cycle of the laser interferometric AC coupled signal. These data acquisition trigger pulses are utilized to sample the non-coherent light interferometer detector signal J at constant-distance intervals. When all of the data acquisition trigger pulses are utilized, the sampling distance interval is $\lambda_c/4$. If smaller sampling intervals are desired, then photodetector 50 could be split into a pair of detectors (not shown) with a 90° phase lag inserted into one of the paths. Then, the signals from the pair of detectors would be sent into further processing electronics, similar to that described above. When the two signals are combined using an or-gate, then data acquisition trigger pulses would be available at a sampling interval of $\lambda_c/8$. Alternatively a divide-by-n circuit could be included to decrease the number of data acquisition trigger pulses to some multiple $n\lambda_c/4$, where n is a small integer.

Figure 9:
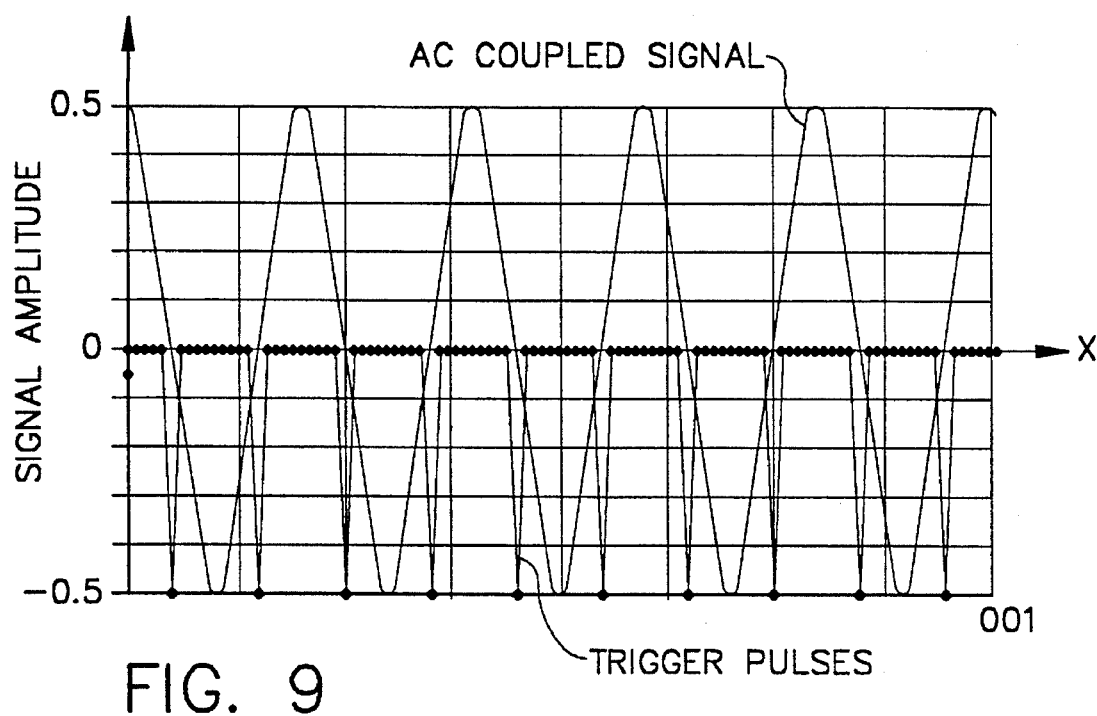
FIG. 9 illustrates AC coupled signals from FIG. 8 data along with data acquisition trigger pulses derived from the AC coupled signals.

FIG. 9 shows an example of the AC coupled signal along with the data acquisition trigger pulses produced at each zero crossing. A comparator with hysteresis can be utilized to obtain data acquisition trigger pulses at points other than the zero crossings on each cycle of the coherent light signal.

A discussion of interference of partially-coherent light is found in B. E. A. Saleh and M. C. Teich, *Fundamentals of Photonics*, John Wiley & Sons, Inc., NY, 1991, pages 360–366. LED 14 of non-coherent light interferometer 53 is considered a partially-coherent source by the above reference. When two partially-coherent light beams interfere, the non-coherent light interferometer detector signal J detected by photodetector 32 is given by the relationship:

$$J(x) = J_O + J_R + 2\sqrt{J_O J_R} \; |g_{sr}(x)|\cos\phi(x) \quad (2)$$

where x is the position of retroreflector 48 relative to a reference position $x_o$;

J(x) is the non-coherent light interferometer detector signal as a function of position x;

$J_o$ is the signal intensity of the object branch of non-coherent light interferometer 53;

$J_R$ is the signal intensity of the reference branch of non-coherent light interferometer 53;

$g_{sr}(x)$ is a normalized mutual coherence function; and $\phi(x)$ is the phase difference between the two light signal intensities, i.e., $J_o$ and $J_R$.

For LED light sources, the coherence function $g_{sr}(x)$ is a Gaussian function of x. The position of mutual coherence for each interface is defined as the location of the central maximum in the non-coherent light interference signal. In the case where the light signal from the object branch and reference branch are mutually coherent at location $x_p$, the third term in Equation 2 (called the interference signal) can be written as follows:

$$S(x) = J_S e^{-k(x-x_p)^2} \cos\left(\frac{4\pi(x-x_p)}{\lambda_N}\right) \quad (3)$$

where

S(x) is the interference signal from Equation 2;

$J_S$ is the maximum detected signal strength of non-coherent light interferometer 53 at photodetector 32;

k is a constant which is related to the source coherence length;

$x_p$ represents a position at which maximum constructive interference occurs; defined as a location of retroreflector 48 corresponding to an optical interface in object 25 wherein the optical path lengths of the object branch and the reference branch of non-coherent light interferometer 53 are equal;

x is the x-coordinate of retroreflector 48; and $\lambda_N$ is the center wavelength of non-coherent light source LED 14.

The source coherence length of non-coherent light source LED 14 is given by the relationship:

$$L_C = \frac{2\ln 2 \lambda_N^2}{\pi \Delta \lambda_N} \quad (4)$$

where $L_C$ is the LED source coherence length; and $\Delta\lambda_N$ is the bandwidth of non-coherent light source LED 14.

The coherence length defines the full width at half maximum of the Gaussian function in Equation 3. When x−xp=

$L_C/2$, the normalized Gaussian function is equal to ½. The value of k which satisfies this relationship is:

$$k = \frac{4\ln 2}{L_C^2} = \frac{\pi^2(\Delta\lambda_N)^2}{\ln 2(\lambda_N)^4} \quad (5)$$

For example, for a LED having a 1300 nm wavelength with a 60 nm bandwidth, the coherence length is calculated to be 12.429 µm and $k=1.794747\times 10^{10}/m^2$.

Signal Processing and Data Reduction

In order to relate the above discussion regarding data sampling to the determination of physical properties of object 25, a discussion is now presented relating to the processing and data reduction of sampled data sets. For purposes of this discussion, it is assumed that data will be collected sequentially while the position of motor 30 is changed monotonically. It is noted that the positions $x_p$ are defined as locations at which optical interfaces in the object occur. Since the data is sampled at constant distance intervals, the true location of this optical interface will not in general occur at the location of any of the sampled data points. In a manufacturing or industrial environment, there are also a variety of mechanical and electrical noise sources. These noise sources can degrade measurement precision. Therefore, an attribute of the present invention is to locate the center position $x_p$ of the optical interface with a high degree of precision using data sampled in the presence of noise.

In the present invention, sampling is done at constant distance intervals which allows the data to be analyzed by a number of techniques. The main function of signal processing and data analysis is to locate the true position of an optical interface of object 25 in the presence of noise. This reduces mathematically to locating the true position $x_p$ of the interference term $S(x)$ of Equation 3:

$$S(x_i) = J_S e^{-k(x_i - x_p)^2} \cos\left(\frac{4\pi(x_i - x_p)}{\lambda_N} + \phi_o\right) + \text{NOISE} \quad (6)$$

where $S(x_i)$ are the sampled amplitudes of non-coherent interferometer 53;

$x_i$ are the locations of the sampled data points;

$J_S$ is the maximum detected signal strength of the non-coherent light interferometer at photodetector 32;

$\lambda_N$ is the center wavelength of non-coherent light source LED 14;

$\phi_o$ is the phase angle; and

NOISE is the noise term.

Figure 10:
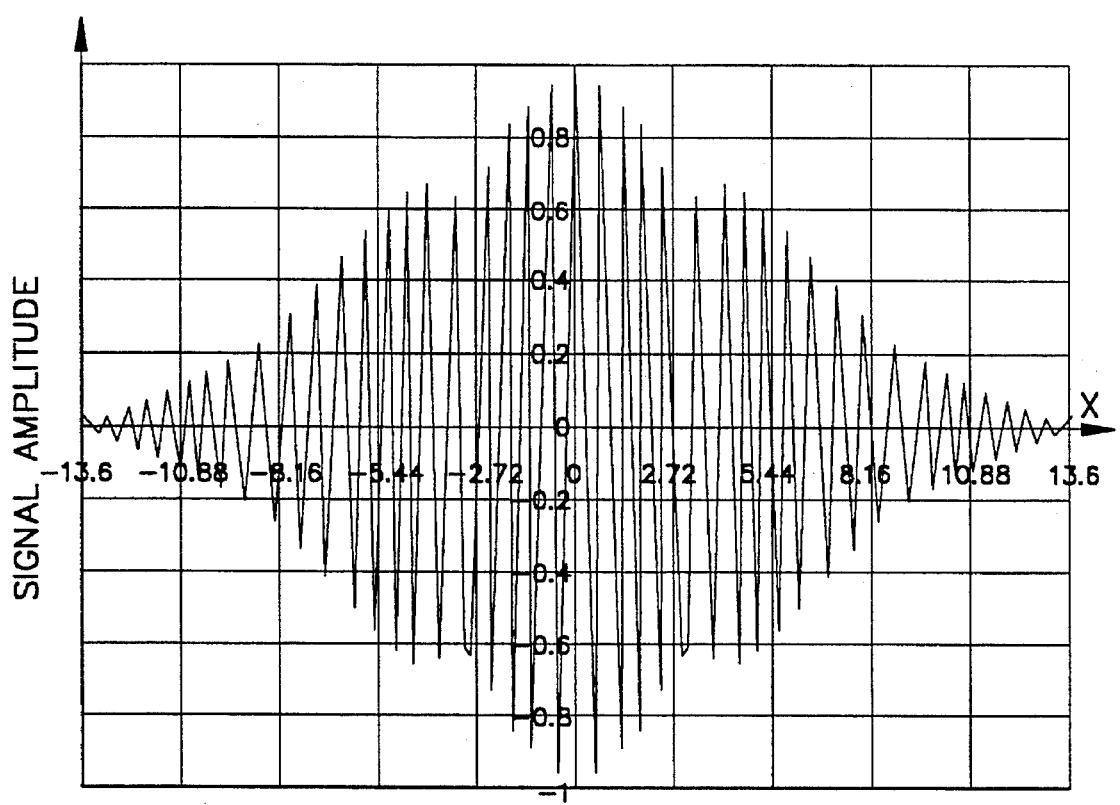
FIG. 10 shows an example of a non-coherent light interferogram.
Figure 11:
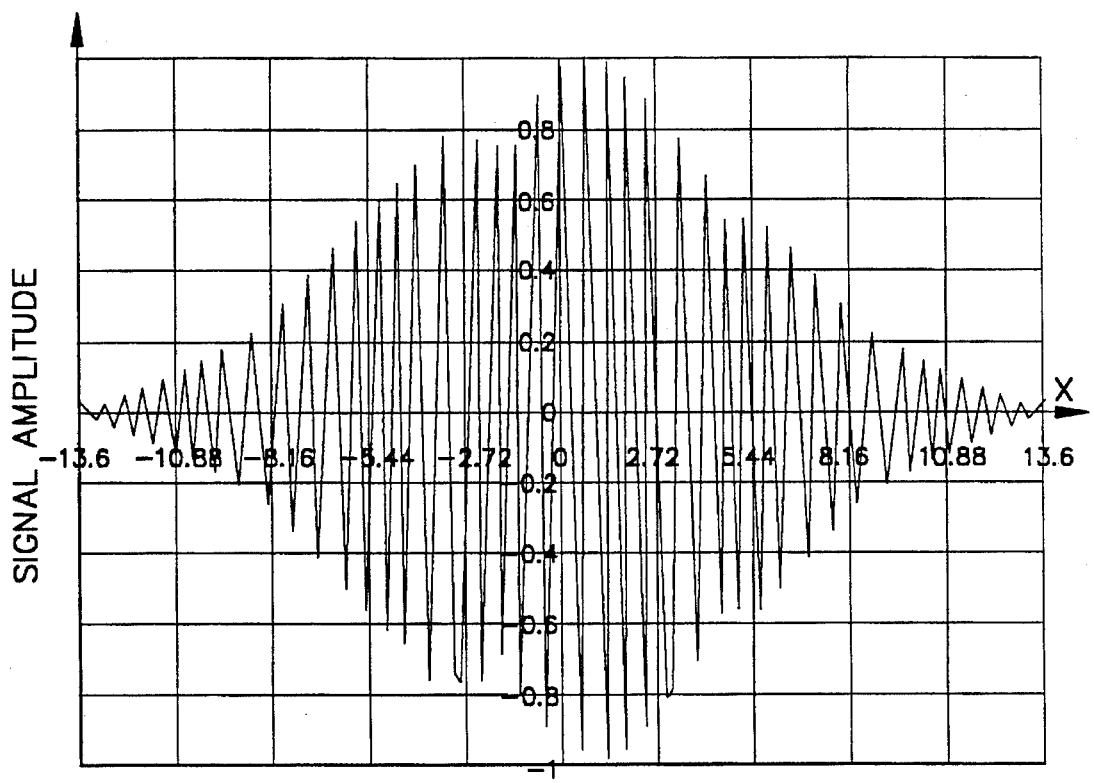
FIG. 11 shows another example of a non-coherent light interferogram.

The phase angle $\phi_o$ is included since the sampling is rarely performed symmetrically around the exact location of the central maximum $x_p$. FIG. 10 shows the calculated signal $S(x_i)$ as a function of x from Equation 6 for a 60 nm bandwidth LED operating at 1300 nm with a sampling interval of $\lambda C/4$ of a 632,991 nm HeNe laser where NOISE=0, $x_p=0$, and $\phi_o=0$. In contrast, FIG. 11 shows the calculated signal $S(x_i)$ as a function of x from Equation 6 using the same source and sampling interval where NOISE=0, $x_o=0$, and $\phi_o=0.5$ radian. Comparing FIG. 10 and FIG. 11, it is evident that an attribute of data analysis is to determine the location of the true center of the Gaussian envelope from a set of data which is not sampled symmetrically around the central maximum, and typically is sampled in the presence of noise. The random noise $\text{NOISE}_R$ is defined as follows:

$$\text{NOISE}_R = \text{noise} * \text{RANDOM} - \frac{\text{noise}}{2} \quad (7)$$

where noise is a noise level constant; and

RANDOM is a random number between 0 and 1.

Figure 12:
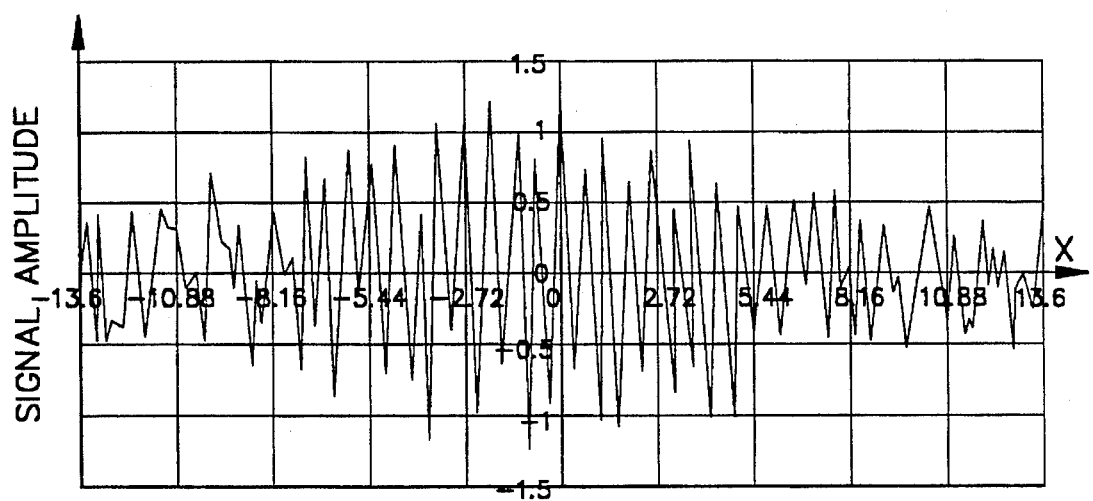
FIG. 12 shows an example of a noisy interferogram of an optical interface.

For example, FIG. 12 shows data, collected using $\phi_C/4$ sampling in the presence of a noise level of 1.0 of an optical interface obtained using a system having a HeNe laser and a 1300 nm LED with a 60 nm bandwidth.

One approach to analyzing such an interferogram is now described. The absolute values of $S(x_i)$ are first calculated. This is followed by performing an m point Gaussian-weighted average given by the relationship:

$$V(x_i) = \sum_m e^{-z(m\Delta x)^2} |S(x_{i+m})| \quad (8)$$

where m is a coefficient which ranges from integer $-q/2$ to $+q/2$;

$q+1$ equals the number of points in the summation;

$\Delta x$ is the sampling interval; and z is a Gaussian filter constant.

Figure 13:
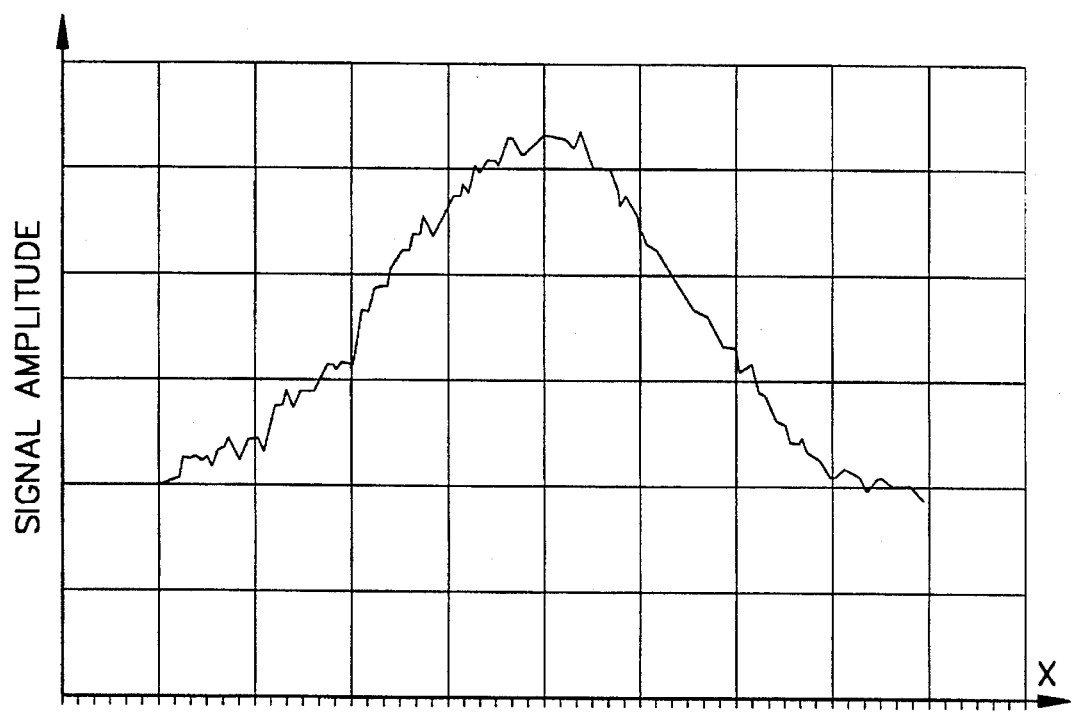
FIG. 13 shows the resultant Gaussian envelope derived from the noisy interferogram of FIG. 12 after signal processing.

FIG. 13 shows a plot of $V(x_i)$ for the data set shown in FIG. 12 where $z=0.06$ and $q=39$ points. To find the true center of the data set, the location of the maximum value of $V(x_i)$ is found and regression analysis is utilized to fit the data set around peaks to the relationship:

$$V(x_i) = A e^{-k(x_i - x_p)^2} \quad (9)$$

where

A is an amplitude constant; and $x_p$ is the calculated location of the peak of the interferogram.

Figure 14:
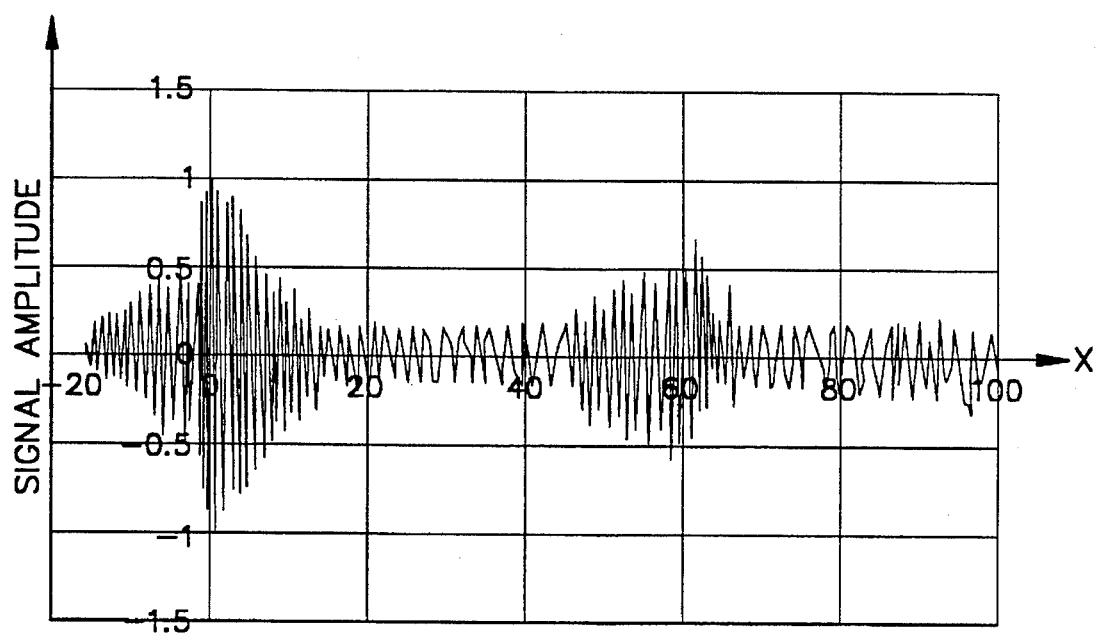
FIG. 14 shows a complete data scan for a 60 micron thick optical path object.
Figure 15:
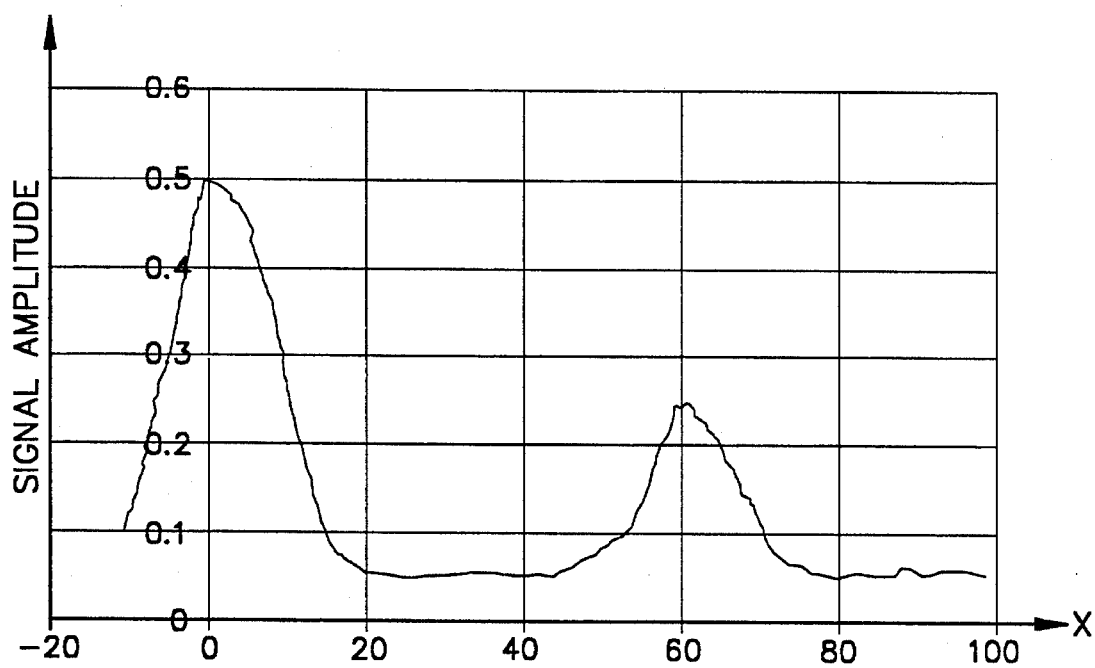
FIG. 15 shows the corresponding Gaussian window envelope calculation obtained on the data of FIG. 14.

Using this relationship, the best fit for the value of $x_p$ can be determined. Measurement repeatability of better than ±0.3 µm has been achieved using this technique. For example, FIG. 14 shows a typical measurement interferogram for a 60 µm thick optical path object, while FIG. 15 shows results of the corresponding Gaussian window envelope calculation obtained using Equation 8.

Measurement System

Figure 16:
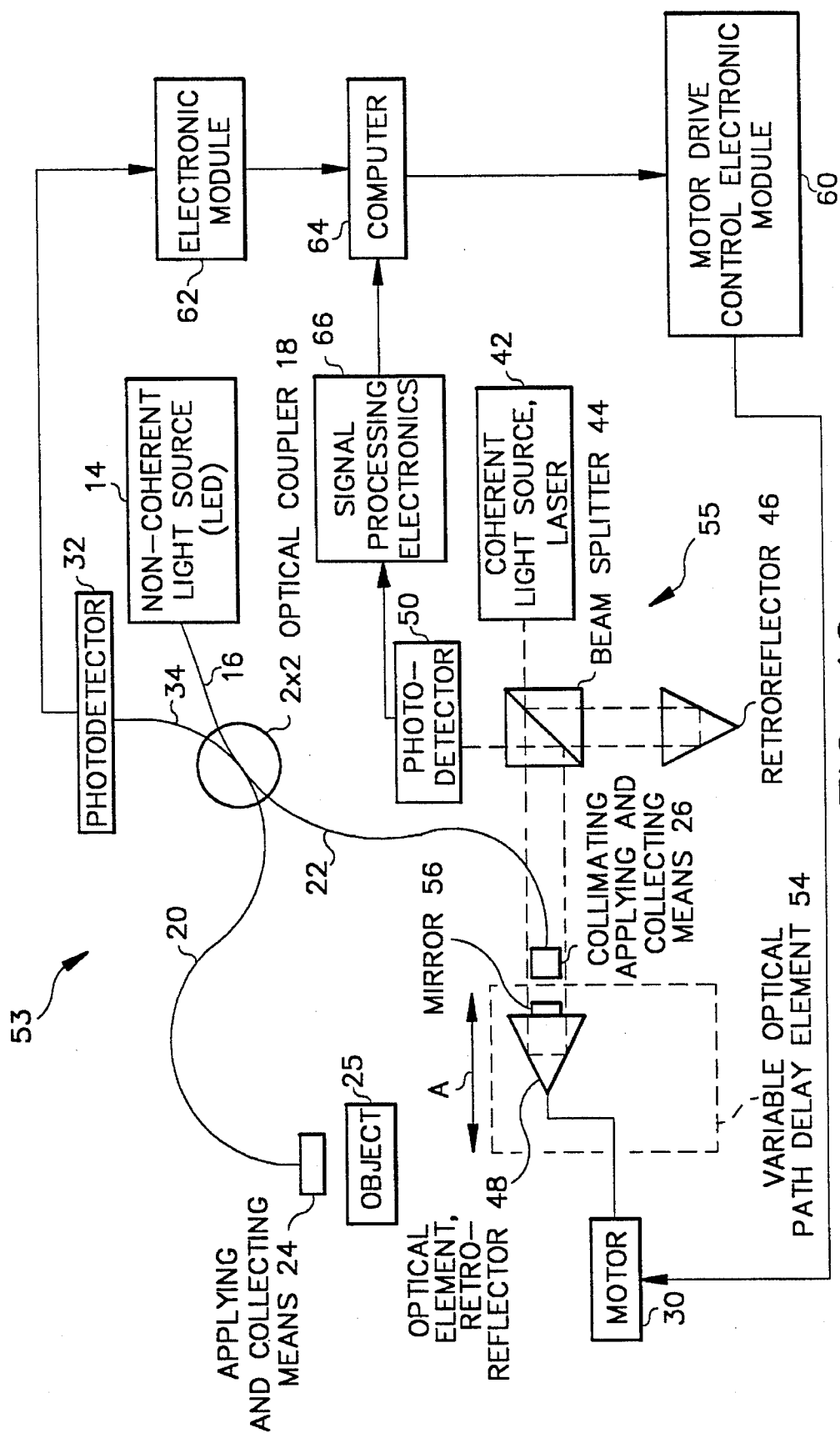
FIG. 16 shows a preferred embodiment of the complete measurement apparatus of the present invention.

FIG. 16 shows a preferred embodiment of the complete measurement system of the present invention. This system includes standard-mode apparatus 52 (as shown in FIG. 4), the control electronics, and the computerized data acquisition system. The measurement system shown in FIG. 16 makes measurements of physical parameters of an object with constant-distance sampling intervals equal to $n\lambda_C/4$, where n is a small integer, and $\lambda_C$ is the wavelength of the coherent light source, laser 42.

As described above with respect to standard mode apparatus 52, the measurement system of the present invention includes coherent light interferometer 55 and non-coherent light interferometer 53 sharing common movable optical path delay element 54. In a preferred embodiment, LED 14 is a 60 nm bandwidth 1300 nm LED of optical power level of 0.1–10 µW coupled into a single-mode fiber by pigtailing. Preferably, the single-mode fiber is composed of Corning SMF-28 grade optical fiber. The light signal from LED 14 is split into the third and fourth light signals by 2×2 optical coupler 18, such as a GOULD 50/50 single mode optical coupler. The third light signal is incident on object 25. Photodetector 32 is preferably a GaAs semi-conductor photodiode. Laser 42 is preferably a single mode HeNe laser or alternatively a temperature stabilized single mode diode laser such as a Laser Max MDL-200 675 nm laser diode. Beam splitter 44 is preferably a 1.25 cm (½ inch) or 2.5 cm (1.0 inch) diameter beam splitter cube. Retroreflectors 46 and 48 are preferably corner-cube retroreflectors or hollow retroreflectors. Photodetector 50 is preferably a silicon photodiode.

In situations where a fiber probe can be located within a distance of 1–15 mm of the front surface of object 25, separate coupling optics (for example, applying and collecting means 24) to object 25 are not required. A single-mode optical fiber termination cleaved normal to the light propagation direction can be used as the coupler optics to provide a reference reflection from the fiber-to-air interface. Reflected light from object 25 is coupled back into non-coherent light interferometer 53 by means of the same single-mode optical fiber 20. Having a reference reflection from the probe-to-air interface is especially useful in surface profiling applications and in applications where measurement of distance to a surface is critical.

In a preferred embodiment utilizing coupling optics, the coupling optics consist of an angle-cleaved single-mode fiber offset from a Nippon Sheet Glass (NSG) SLW 3 mm diameter, 0.11 pitch, NA 0.46 (on axis) gradient index (GRIN) lens housed together in an optical mount. No reference reflection at the optical fiber-to-air interface is observed in this embodiment. The focal length, depth of focus, and angular field of view can be adjusted by varying the distance between the angle-cleaved-fiber and the lens. For the case of a 4.9 mm offset, the focal length is 25.5 mm, with a depth of focus of 2.2 mm and an angular field of view of 0.95 degrees FWHM. Reflected light from object 25 is coupled back into non-coherent light interferometer 53 by means of the same coupling optics.

Preferably, variable optical path delay element 54 includes a prism retroreflector and a mirror mounted on the diaphragm cone of a moving-coil loudspeaker; the mirror being mounted On a portion of the surface of the prism retroreflector. An example of the moving coil loudspeaker is a REALISTIC 8 inch (20 cm) Sub-woofer with a maximum peak-to-peak excursion of about 20 mm. The motion of the moving coil loudspeaker is controlled by motor 30, which the magnet-coil assembly in the loudspeaker. As the loudspeaker cone moves, the optical path lengths of the reference branch of coherent light interferometer 55 and non-coherent light interferometer 53 change by the same amount. The optical path length of common variable optical path delay element 54 is preferably varied using motor drive control electronic module 60 comprising a function generator and power amplifier, thereby controlling the current to the loudspeaker coil.

The fourth light signal emanating from 2×2 optical coupler 18 and traveling down single-mode optical fiber 22 is collimated by a collimating lens, shown in FIG. 16 as collimating applying and collecting means 26, which is similar to that of the preferred object coupling optics described above with the exception that a collimating lens is utilized. While the second light signal (from laser 42) is incident onto retroreflector 48, the fourth light signal (from LED 14) is incident onto mirror 56; mirror 56 being co-mounted with retroreflector 48. The reflected non-coherent light signal is also collected by collimating applying and collecting means 26. After passing back through single-mode optical fiber 22 to 2×2 optical coupler 18, the combined non-coherent light signal is coupled through single-mode optical fiber 34 to photodetector 32. The analog output of photodetector 32 is amplified and filtered by an electronic module 62, digitized at constant distance intervals by utilizing the coherent light interferometer data acquisition trigger pulses (as described below), and analyzed by a computer system 64, such as a PC containing a National Instruments AT-MIO-16X, 16-bit, 100 KHz data acquisition board or a EISA A-2000, 12-bit, 1 MHz data acquisition board operating in a LabWindows (TM of National Instruments) environment. The non-coherent light interferometric data are then digitized at constant distance intervals.

As described above, the photodetector 50 signal I is input into and processed by a signal processing electronics 66 to create data acquisition trigger pulses. The photodetector signal I is AC coupled and fed into a comparator which detects zero voltage crossings or some (i.e., one or more) other reproducible locations on each cycle of the laser interferometic AC coupled signal. The comparator outputs are utilized to create negative going data acquisition trigger pulses at constant distance intervals. As such, laser interferometer 55 is utilized to trigger analog-to-digital conversion of the amplified signal from photodetector 32, and to provide digitized data at constant distance intervals of $n\lambda_c/4$ as described above. For n=1 with a 632.991 nm HeNe laser, data are acquired at 0.15825 μm intervals.

During typical operation, motor 30 is driven with a 1–100 Hz sine wave, depending on the total amplitude and measurement rate required to analyze object 25. In a preferred embodiment incorporating the moving coil loudspeaker, the moving coil will alternately monotonically increase and monotonically decrease the optical path length of common variable optical path delay element 54 in the reference branches of interferometers 53 and 55 by a distance sufficient to determine the physical property of object 25. If the physical property of interest is optical thickness, the distance traveled by variable optical path delay element 54 must be greater than the optical thickness of object 25. Measurements can be made while variable optical path delay element 54 is moving in either direction. Thus, two measurements of the thickness of object 25 can be made for each cycle of the moving coil loudspeaker. Multiple measurement cycles are performed by driving the moving coil loudspeaker coil with a repetitive waveform. No home reference position of moving coil loudspeaker (i.e., motor 30) is required to determine the physical property of the object since the absolute motor position is not utilized in the analysis.

Preferably, the position at which the two optical path lengths of the object branch and the reference branch of non-coherent light interferometer 53 are equal, should be near the center of the scan. To accomplish this, the optical path length from optical coupler 18 to the first surface of object 25 (i.e., the surface closest to applying and collecting means 24) should be greater than the shortest optical path length of the reference branch (of non-coherent light interferometer 53) during a scanning cycle. Further, the optical path length from optical coupler 18 to the second surface of object 25 (i.e., the surface farthest from applying and collecting means 24) should be less than the longest optical path length of the reference branch during a scanning cycle.

Figure 17:
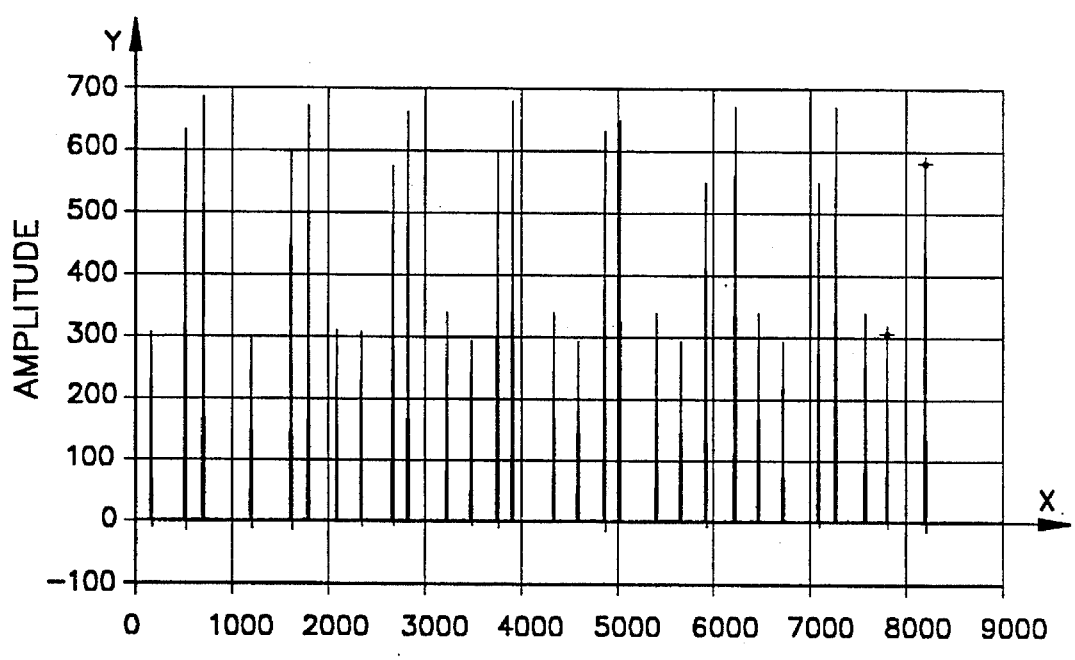
FIG. 17 shows repetitive scan data of a glass plate object.

FIG. 17 shows data obtained using a 10 Hz sine wave motor drive frequency with a peak-to-peak amplitude of about 1.35 mm obtained using $3\lambda_c/4$ sampling intervals. The data displayed in FIG. 17 are the absolute values of the envelope of the interferograms (y-axis) as a function of total distance scanned during the data acquisition measurement cycle (normalized per unit distance interval between data acquisition events). Object 25 in this demonstration is a 613 μm thick optical flat glass plate with a group index of refraction of 1.4609. A peak is defined as the maximum of the Gaussian envelope of the interferogram at locations of mutual coherence. The first two peaks (due to the reflections from the front and back surfaces of the glass plate, respectively) are obtained while the variable optical path delay element 54 is increasing in optical path length. At a location between the second and third peak, motor 30 changes the direction of motion of variable optical path delay element 54. The third and fourth peaks arising from the second and first surfaces of object 25, respectively, are obtained while the optical path length of the reference branches of interferometers 53 and 55 are decreasing. The scanning cycle continues; at a position between the fourth and fifth peak, motor 30 again changes direction. The thickness of object 25 is determined from the difference in calculated center positions of the first two peaks, and again from the difference in calculated center positions of the third and fourth peaks. Since the distance between the second and third peaks is not utilized in the calculations, the exact location at which motor 30 switches direction is unimportant and does not have to be known in order to perform measurements of physical properties of object 25.

Table 1 summarizes data for repetitive measurements obtained with object 25 being the 613 μm thick optical flat glass plate with a group index of refraction of 1.4609. The first row of data in Table 1 corresponds to the data illustrated in FIG. 17. All thicknesses are in units of μm, m is the number of samples in each data set, and the data are obtained at a rate of 20 Hz using $3\lambda_c/4$ sampling intervals. The individual data sets shown in Table 1 were obtained over a several month period, and the last row in Table 1 shows the average values of the individual data sets. A thickness measurement resolution of ±0.3 μm was demonstrated using the present invention. The data demonstrate that the apparatus is reproducible over extended periods of time without the need for external calibration. Calculated group indices of refraction for the 613 μm thick optical flat glass plate are also tabulated in Table 1.

TABLE 1

Repetitive measurements on a 613 μm thick glass plate.
All thicknesses are in μm, m = number of samples in each data set.

| m | thickness | sigma | range | group index of refraction n |
|---|---|---|---|---|
| 15 | 895.5208 | 0.070647 | 0.221 | 1.46088 |
| 109 | 895.4369 | 0.168216 | 0.585 | 1.46074 |
| 110 | 895.6649 | 0.138653 | 0.4400 | 1.46112 |
| 53 | 895.7310 | 0.153963 | 0.5015 | 1.46123 |
| 107 | 895.4778 | 0.116756 | 0.343 | 1.46081 |
| 100 | 895.3299 | 0.127709 | 0.4265 | 1.46057 |
| 15 | 895.5208 | 0.070647 | 0.221 | 1.46088 |
| 305 | 895.6182 | 0.11028 | 0.4075 | 1.46104 |
| 109 | 895.5964 | 0.116121 | 0.4765 | 1.46101 |
| avg | 895.5471 | 0.131043 | 0.4011 | 1.46093 |

Figure 18:
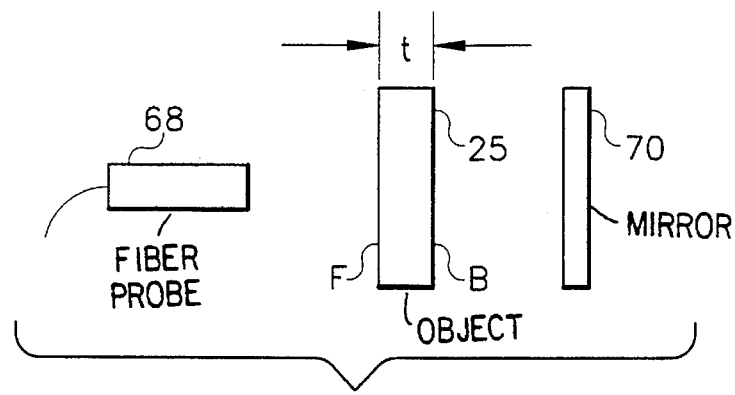
FIG. 18 shows an optical probe arrangement used for index of refraction measurement.
Figure 19:
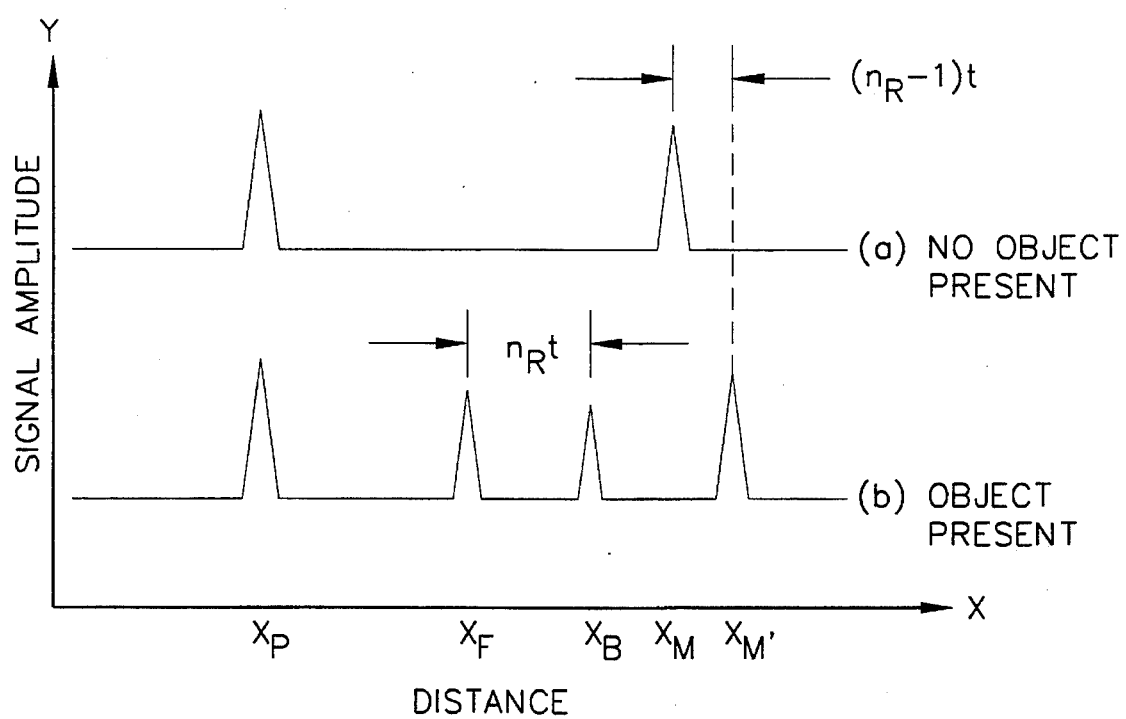
FIG. 19 shows the corresponding mode of operation for the arrangement illustrated in FIG. 18

The arrangement shown in FIG. 18 was used to measure the group index of refraction ($n_R$) of object 25. A normal-cleaved fiber probe 68 was used as the coupling optics to object 25. Object 25 was positioned between fiber probe 68 and a mirror 70. A plot of the corresponding absolute value of the signal amplitude as a function of distance is shown below the arrangement in FIG. 19. If object 25 is not present during a measurement scan, only two reflections are observed as shown in trace (a) of FIG. 19 as $X_P$ and $X_M$. The distance $X_{PM}$ between mirror 70 and fiber probe 68 is given by the relationship:

$$X_{PM} = X_P - X_M$$

When object 25 is present (i.e., when object 25 is inserted into the optical path between fiber probe 68 and mirror 70), the distance $X_{PM}$ is held constant. When object 25 is present, as shown in trace (b) of FIG. 19, four reflections are observed at the following locations: the observed reflection from fiber probe-to-air interface ($X_P$), the observed reflection from air-to-front surface F of object 25 interface ($X_F$), the observed reflection from back surface B of object 25 to air interface ($X_B$), and the observed reflection from air-to-mirror 70 interface ($X_{M'}$). The relationships between these locations are:

$$n_R t = X_B - X_F$$

$$(n_R - 1)t = X_{PM'} - X_{PM}$$

$$t = X_B - X_F - (X_{PM'} - X_{PM})$$

where t is the thickness of object 25, and $X_{PM'}$ is the observed distance between fiber probe 68 and mirror 70 with object 25 inserted into the optical path. Note that the group index of refraction ($n_R$) and the thickness (t) of object 25 can be calculated from the above relationships.

Autocorrelation Apparatus

Figure 20:
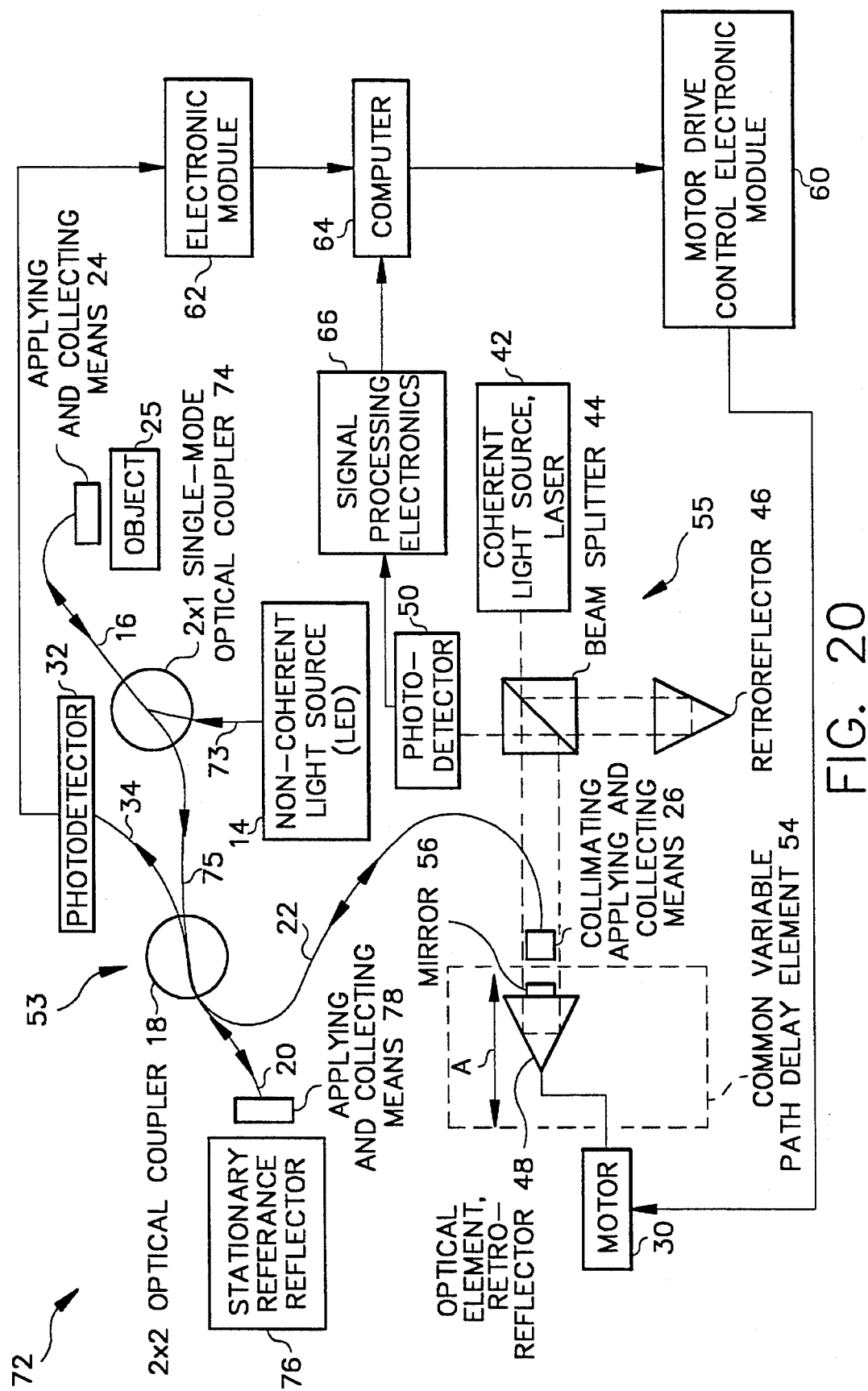
FIG. 20 shows a fifth embodiment of a dual interferometer apparatus of the present invention, referred to as the optical autocorrelation mode apparatus.

FIG. 20 shows a further embodiment of the present invention, which will hereinafter to referred to as the optical autocorrelation mode apparatus 72. A distinction between autocorrelation mode apparatus 72 and previously described standard mode apparatus 52 is the placement of object 25. In autocorrelation mode apparatus 72, object 25 is positioned in the light source branch of non-coherent light interferometer 53 (i.e., input), rather than being positioned in one of the interfering branches. As shown in FIG. 20, a light signal from LED 14 is coupled to object 25 by means of an optical fiber 73 through a 2×1 single mode optical coupler 74 into optical fiber 16 and applying and collecting means 24. Applying and collecting means 24, as used in standard mode apparatus 52, is used to illuminate and collect reflected light from object 25. The light reflected from object 25 passes back through optical fiber 16 and the 2×1 single-mode optical coupler 74 back into a single-mode optical fiber 75. This signal passing through optical fiber 75 (herein called the object signal) is split into third and fourth light signals at 2×2 optical coupler 18. The third light signal is directed to a second stationary reference reflector 76 through collimating applying and collecting means 78. Alternatively, single-mode fiber 20 can be terminated with a normal cleaved mirrored surface at its tip (not shown) in place of collimating applying and collecting means 78 and second stationary reference reflector 76. A portion of the third light signal is reflected back from second stationary reference reflector 76 into collimating applying and collecting means 78, and is coupled back into single mode optical fiber 20. This signal is referred to as the second reference signal. The fourth light signal, traveling along single-mode optical fiber 22, is incident on collimating applying and collecting means 26, which collimates the fourth light signal. Collimating applying and collecting means 26 applies the fourth light signal to mirror 56 mounted onto retroreflector 48 of common variable optical path delay element 54. A portion of the fourth light signal is reflected back from mirror 56 into collimating applying and collecting means 26 and is coupled back into single-mode optical fiber 22. This signal is referred to as the second delay signal. The optical path from optical coupler 18 to stationary reference reflector 76 and back to optical coupler 18 is defined as the optical path length of the second stationary reference branch of non-coherent light interferometer 53. Note that the alternative configurations for variable optical path delay element 54 as previously illustrated for standard mode apparatus 52, also apply to autocorrelation mode apparatus 72.

In operation, the third and fourth light signals traveling along single-mode optical fibers 20 and 22, respectively, are reflected back to optical coupler 18 (as the second reference signal and second delay signal, respectively) where they recombine and interfere with each other. A portion of the recombined second reference signal and second delay signal is directed into photodetector 32 by single-mode optical fiber 34.

In autocorrelation mode apparatus 72, constructive interference of the non-coherent light signals occurs when the optical path lengths of the movable reference branch of non-coherent light interferometer 53 and the stationary reference branch of non-coherent light interferometer 53 are equal. Constructive interference of the non-coherent light signals also occurs when these two optical path lengths differ by the optical path length of a physical property of object 25, such as the product of the thickness and the group index of refraction.

Autocorrelation mode apparatus 72 shown in FIG. 20 transforms a series of optical reflections into distance from an origin peaks. The origin is the self correlation function, and the first peak from the origin is the distance between the two closest peaks. The autocorrelation signal A(d) can be modeled as:

$$A(d) = \frac{\sum_{i=1}^{n} [S(x_i) * S(x_{i+d})]}{\sum_{i=1}^{n} [S(x_i) * S(x_i)]} \quad (10)$$

where $x_i$ are the locations of the sampled data points;

$S(x_i)$ is the signal at each data point location;

n is the number of sampled intervals in a complete scan; and d is the optical delay path between the two branches of the non-coherent light interferometer (i.e., the second stationary reference branch and the movable reference branch) which is equal to 0 when the two optical path lengths are equal. The autocorrelation mode apparatus transforms a series of non-coherent light constructive interference peaks occurring at optical interfaces in the object to distances from a central autocorrelation peak. During an autocorrelation mode apparatus scan, the largest intensity peak (i.e., central autocorrelation peak) occurs when the path lengths of the second stationary reference branch and the movable reference branch are equal.

Figure 21:
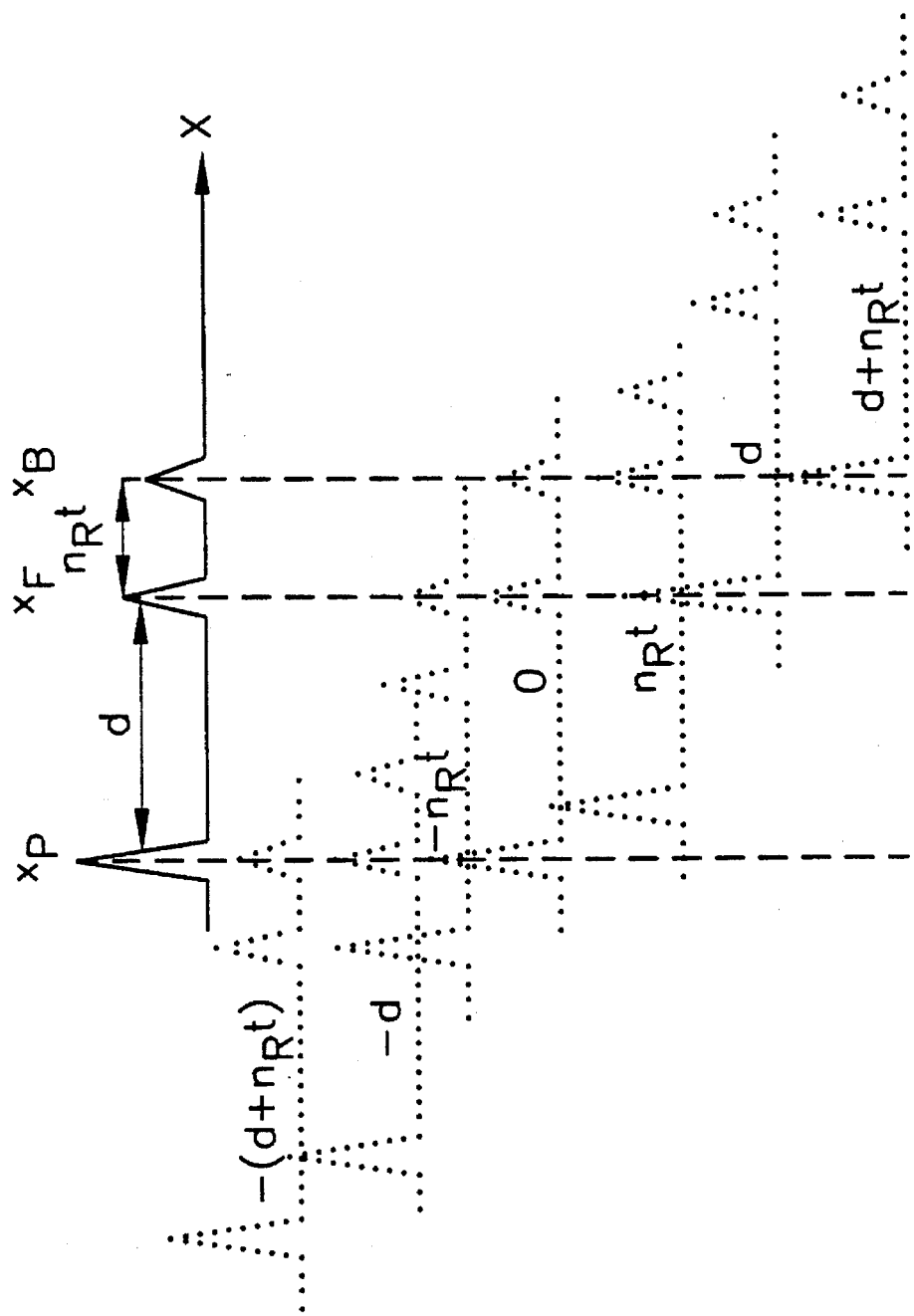
FIG. 21 (a–h) describes the mode of operation for the embodiment shown in FIG. 20.
Figure 22:
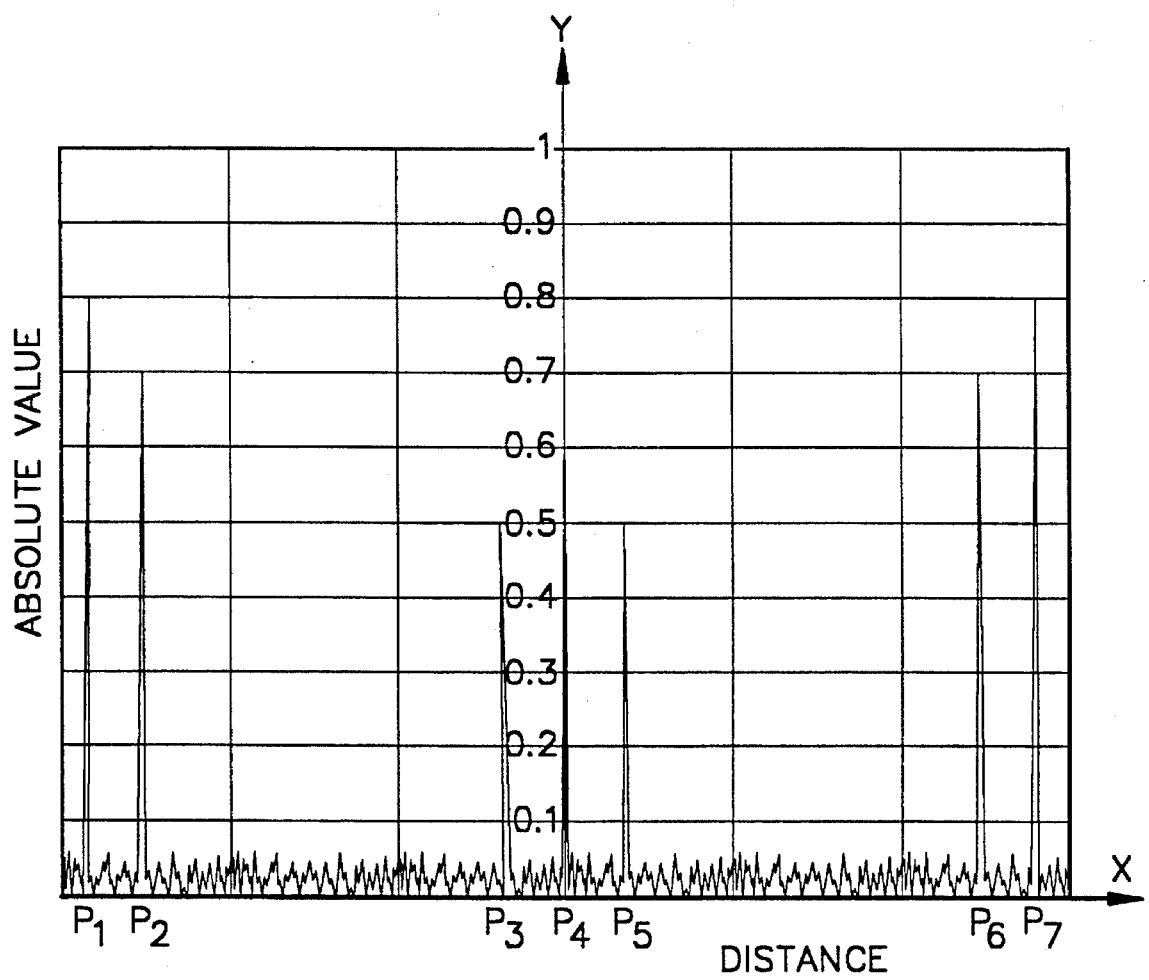
FIG. 22 shows an interferogram obtained with the embodiment shown in FIG. 20.

FIG. 21 is used to explain the appearance of the interferogram shown in FIG. 22; FIG. 22 being obtained using autocorrelation mode apparatus 72 shown in FIG. 20. The sample consists of object 25 having two surfaces, as shown in FIG. 18; a front surface F and a back surface B. Accordingly, a reflection is observed at the location of the front surface and another at the location of the back surface. In addition there is a reflection observed at the location of the optical fiber probe-to-air interface. Trace (a) of FIG. 21 shows the absolute value of the envelope of an optical pulse train in the stationary branch of autocorrelation mode apparatus 72. Three reflections are observed: a reflection from the optical probe ($X_P$), a reflection from the front surface F of object 25 ($X_F$), and a reflection from the back surface B of object 25 ($X_B$). Traces (b) through (h) of FIG. 21 show the absolute values of the envelopes of the optical pulse trains in the movable reference branch as a function of the position of variable optical path delay element 54. The distance d is the distance between the probe tip ($X_P$) and the front surface F of object 25. The value of optical thickness nt is given by the relationship:

$$n_R t = X_B - X_F$$

where n is the group index of refraction and t is actual thickness of object 25. As shown in trace (b) of FIG. 21, when the movable reference branch is at a position $-(d+n_R t)$, the stationary branch peak from the optical probe-to-air interface (at $X_P$) will constructively interfere with the movable reference branch peak associated with the back surface B of object 25. This peak corresponds to the leftmost peak ($P_1$) shown in FIG. 22 obtained using $3\lambda_c/4$ sampling intervals. As the optical path of the movable reference branch is increased, the next location of constructive interference will occur when the movable reference branch is at location $-d$, as shown in trace (c) of FIG. 21. At this location of $-d$, the stationary branch peak from the optical probe ($X_P$) constructively interferes with the movable reference branch peak from the front surface F of object 25. In FIG. 22, the second peak from the left ($P_2$) corresponds with this location of $-d$. As the optical path of the movable reference branch is further increased, the next location of constructive interference of $-n_R t$ is reached, as shown in trace (d) of FIG. 21. At this location of $-n_R t$, the stationary branch peak from the front surface F of object 25 ($X_F$) constructively interferes with the movable reference branch peak from the back surface B of object 25. This location of $-n_R t$ corresponds to peak $P_3$ of FIG. 22. Likewise, as the optical path of the movable reference branch is increased, the next location of constructive interference will occur at X=0 (i.e., where the optical path lengths of the stationary branch and movable reference branch are equal), as illustrated in trace (e) of FIG. 21. At this location, the largest intensity amplitude peak occurs in FIG. 22, at $P_4$. Continuing to increase the optical path of the movable reference branch similarly results in traces (f), (g) and (h) of FIG. 21, which respectively correspond with peaks $P_5$, $P_6$, and $P_7$ of FIG. 22.

If only the optical path length nt of object 25 is to be measured, it is not necessary to scan the full distance from $-(d+n_R t)$ to $+(d+nt)$. Rather, it is only necessary to scan a distance greater than nt so as to include a minimum of two peaks. For example, options are to use the following two sets of peaks from FIG. 22: peaks P1 and P2; peaks P3 and P4; peaks P4 and P5; or peaks P6 and P7.

It is not required to have a reflection from the optical probe to measure the optical path nt of object 25 having two surfaces. In this case, only three peaks would be observed in a single scan, which would be equivalent to the central three peaks of FIG. 22 (i.e., $P_3$, $P_4$, and $P_5$). These peaks correspond, respectively, to the interference coincidences shown in traces (d), (e), and (f) of FIG. 21.

Figure 23:
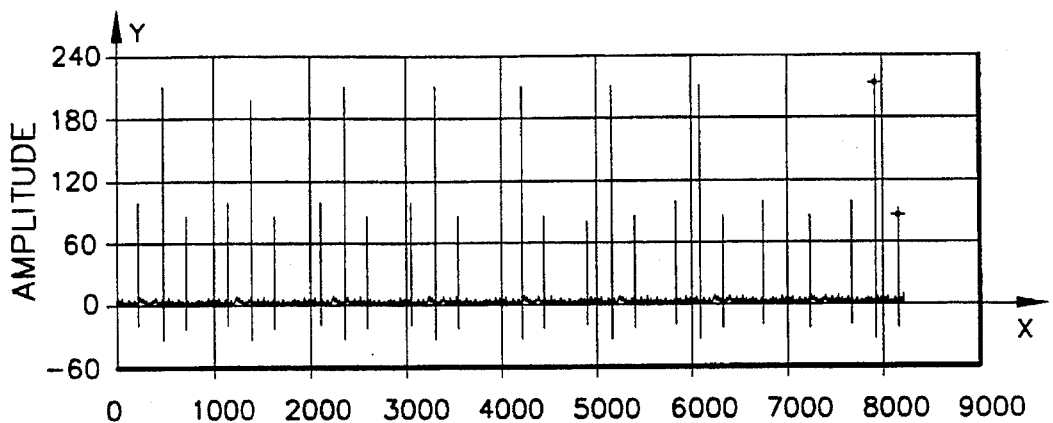
FIG. 23 shows repetitive scan data obtained with the embodiment shown in FIG. 20.

An example of repetitive scan data obtained with optical autocorrelation mode apparatus 72 applied to measuring optical path thickness of object 25 is shown in FIG. 23. FIG. 23 shows a display of the absolute value of the envelope obtained while measuring a 613 μm glass plate as a function of motor scan distance for the apparatus shown in FIG. 20. The x axis is displayed as sample distance intervals (1 unit=$\lambda_c/4$=0.15825 μm). The data in the figure was obtained using $3\lambda_c/4$ sampling intervals. At x=0, the non-coherent light interferometer optical path length for the movable branch was shorter than the stationary reference branch. The first three peaks from the left end of FIG. 23 were obtained while the optical path length of the movable branch was being increased. The first peak occurs when the path length of the movable branch is shorter than the stationary reference branch by the optical path thickness of object 25. The second and largest peak occurs when the two path lengths of both interferometer branches are equal. The third peak occurs when the path length of the movable branch is longer than the stationary reference branch by the optical path thickness of object 25. The distance between the first and second peak, and the distance between the second and third peaks are the same; that is, they are equal to the optical path thickness (group index of refraction x thickness) of object 25. At some position past the third peak, the direction of motor 30 is reversed and the fourth through sixth peaks are obtained while the optical path length of the movable branch is decreasing. Here, the fourth peak corresponds to the same relative position as the third peak; the fifth peak corresponds to the second peak; and the sixth peak corresponds to the first peak. Between the sixth and seventh peaks, motor 30 has again reversed direction and the seventh peak is corresponds to the first peak, and the cycle is repeated.

The data in FIG. 23 were obtained using a sine wave drive signal on motor 30 to vary the optical path length of variable optical delay element 54 in the movable reference branch of autocorrelation mode apparatus 72. Other waveforms could be utilized without affecting the results. As in the case of standard mode apparatus 52, there is no need to have a constant velocity motor.

Two sets of measurements are obtained with the standard mode apparatus 52 during each cycle of the sine wave used to excite motor 30, while four sets of measurements are obtained with the autocorrelation mode apparatus 72 during each cycle of the sine wave used to excite motor 30. A DC offset can optionally be utilized to vary the central position of the scan, and the sine wave amplitude can be varied to change the total distance which motor 30 travels during a scan. With autocorrelation mode apparatus 72, it is not necessary to scan the full distance to obtain the three-peak symmetric pattern shown in FIG. 23. The DC offset and sine wave amplitude can also be adjusted so that only the central peak and one side peak of the triplet of peaks are obtained during each half of the sine wave cycle. The resulting data would then appear similar to that shown in FIG. 17.

Figure 24:
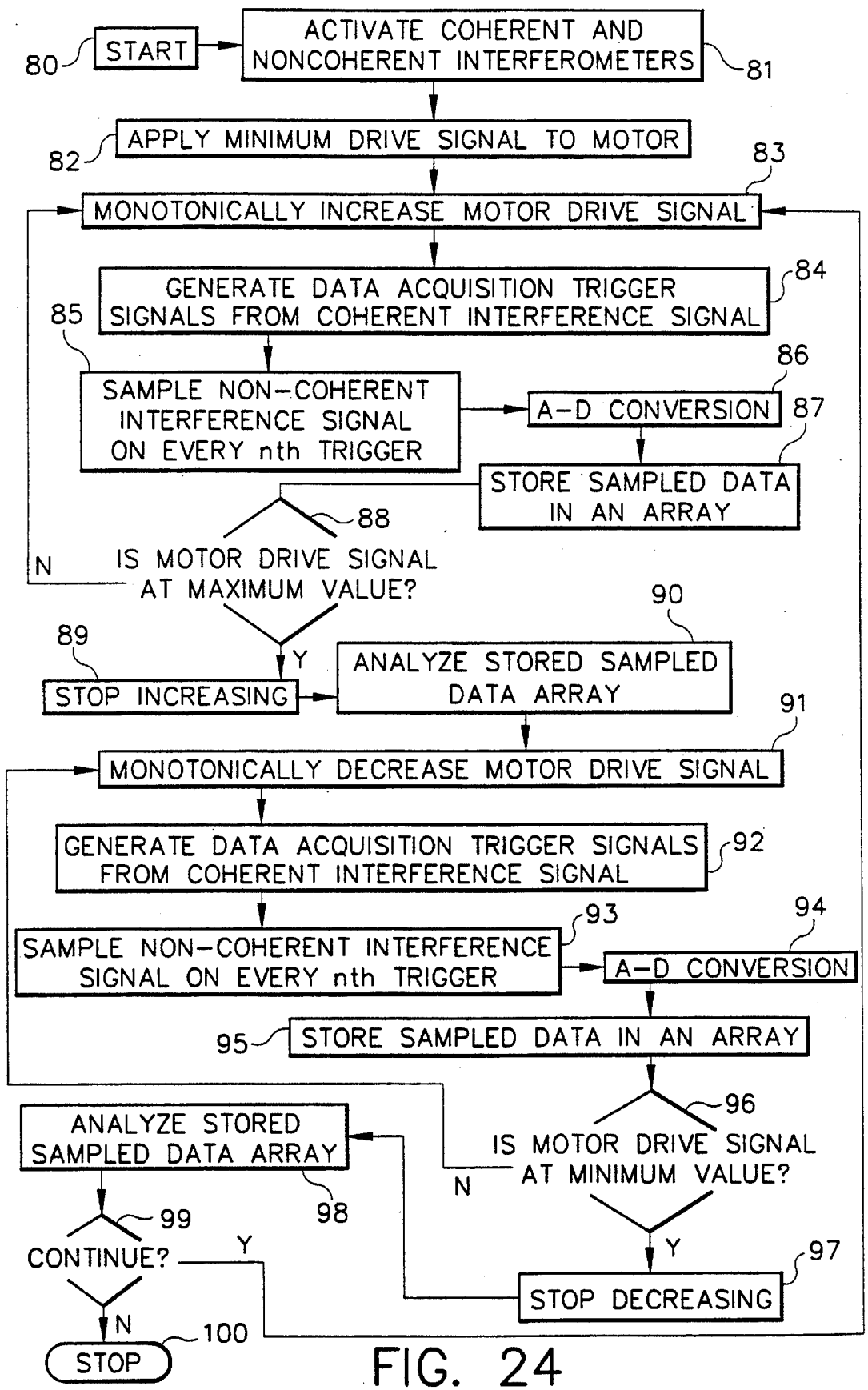
FIG. 24 shows a flow chart which summarizes a first approach to obtaining repetitive measurement data.
Figure 25:
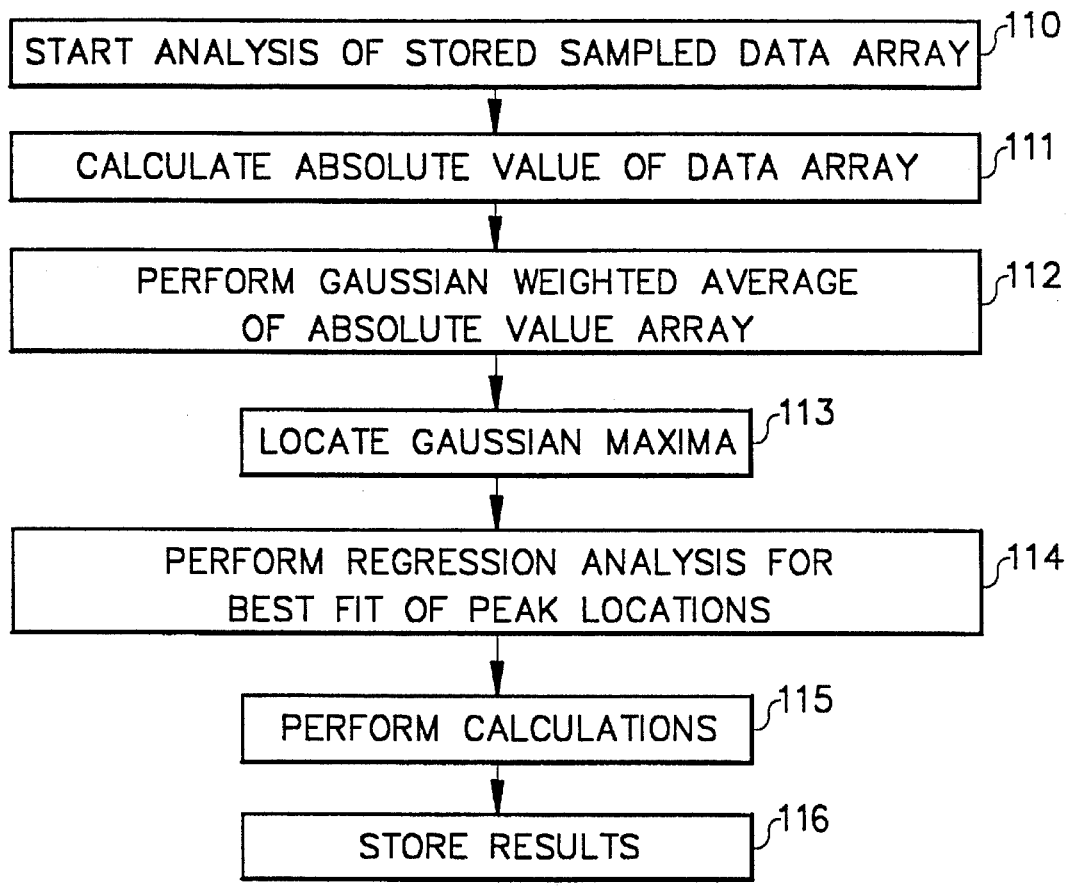
FIG. 25 details a step shown in FIG. 24.

The flow charts in FIG. 24 and FIG. 25 summarize one approach to obtaining repetitive measurement data (as illustrated in FIG. 17 and FIG. 23) to determine physical properties of object 25. As shown in FIG. 24, once a series of repetitive measurement cycles is initiated (80), the coherent and non-coherent interferometers are activated (81) until measurements are complete. The minimum drive signal is applied to motor 30 to position variable optical path delay element 54 at a relative minimum displacement position (82). The motor drive signal is then monotonically increased toward its maximum value (83), thus moving variable optical path delay element 54. Data acquisition trigger signals are generated from the coherent interference signals (84). The data acquisition trigger signals (or a subset) are used to sample the non-coherent interference signal on every nth trigger (85). An A-D conversion is utilized to digitize the sampled analog signal (86), which is then stored in a data array (87) (preferably, a sequential data array). A decision is then made to determine whether the motor drive signal has reached its maximum value (88). If no, steps 84 through 88 are repeated. Once the motor drive signal reaches its maximum value, the motor drive signal is no longer increased (89). The sequential data array is analyzed (90), for example, as described in FIG. 25. The motor drive signal is then monotonically decreased (91) toward its minimum value. Steps 84 through 87 are repeated for this direction of motor travel as shown in steps 92 through 95. A decision is then made to determine whether the motor drive signal has reached its minimum value (96). If no, steps 92 through 95 are repeated. Once the motor drive signal reaches its minimum value, the motor drive signal is no longer decreased (97). The stored sampled sequential data array is then analyzed, for example, as shown in FIG. 25 (98). If further measurements are to be made (99), the cycle is repeated at step 83. If not, the measurement cycle is ended (100).

FIG. 25 shows the details of steps 90 and 98 of FIG. 24. Once the data analysis is initiated (110), the absolute values of the data array elements are obtained (111). Then, a Gaussian-weighted average based on Equation 8 is performed on these absolute values (112). The locations of the maxima of the Gaussian-weighted average are determined (113). Regression analyses are performed on the Gaussian-weighted average data using subsets of data surrounding the locations of the maxima to obtain the best fit to Equation 9 (114) $x_p$. The appropriate calculations are performed to determine the value(s) of the physical property(s) under consideration (115). This data is stored in one or more arrays for further use (116).

Figure 26:
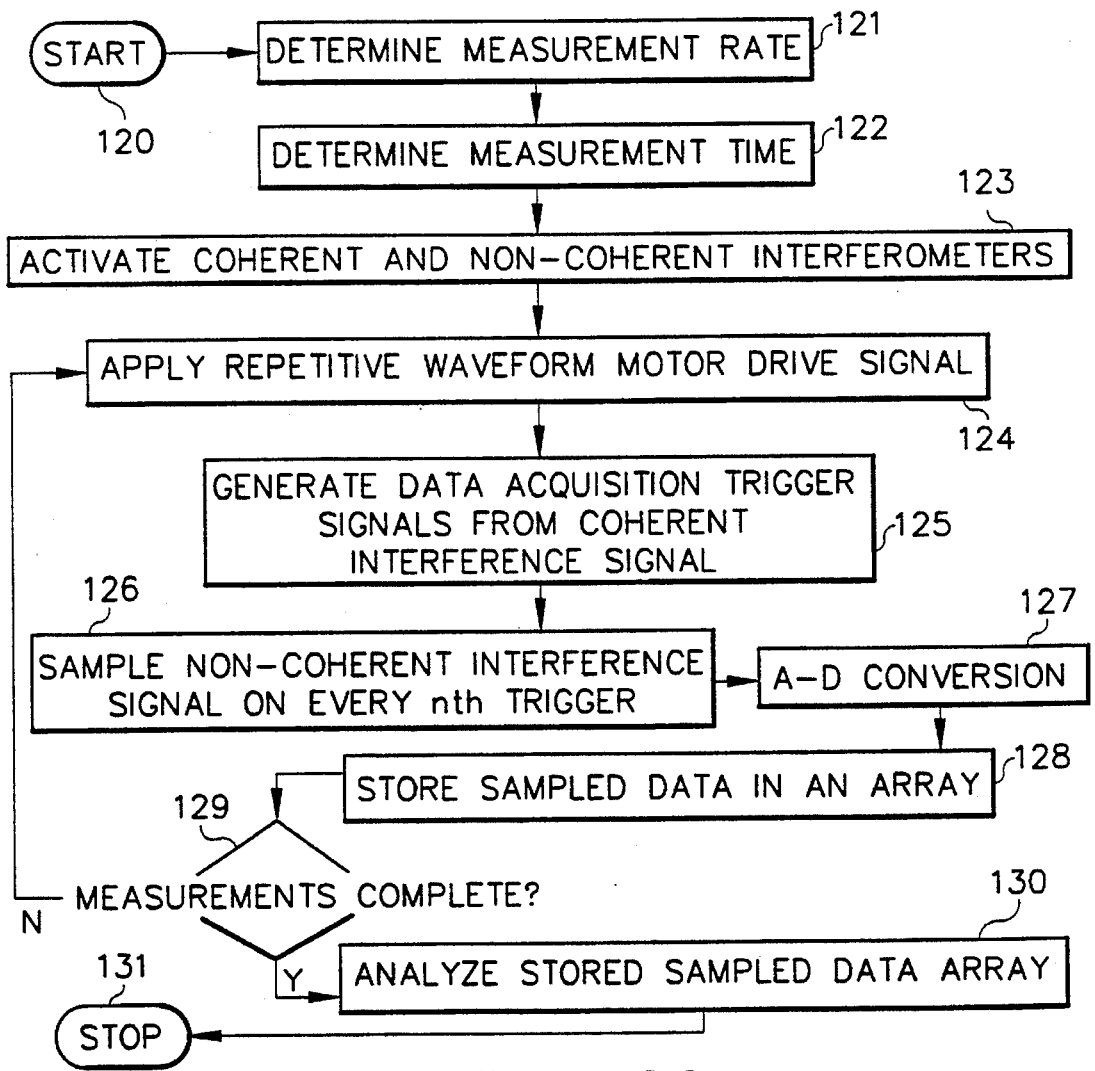
FIG. 26 shows a flow chart which summarizes a second approach to obtaining repetitive measurement data.

The flow chart in FIG. 26 summarizes an alternate approach to obtaining repetitive measurement data (as illustrated in FIG. 17 and FIG. 23) to determine physical properties of object 25. This approach is useful in scanning applications. As shown in FIG. 26, when starting a series of repetitive measurements (120), first the measurement rate (e.g., measurements/second) is determined (121), followed by the total measurement time (e.g., seconds) (122). The coherent and non-coherent interferometers are activated until the measurements are complete (123). A repetitive waveform drive signal (e.g., sine wave) is applied to the motor (124). This repetitive waveform alternately monotonically increases and monotonically decreases the motor position by an amount sufficient to determine the physical property of object 25. This repetitive waveform would have a frequency of ½ or ¼ of the measurement rate from step 121, depending on whether doublets or triplets are obtained (as shown in FIG. 17 and FIG. 23). Steps 125 through 128 are as shown in steps 84 through 87 of FIG. 24. A decision is made as to whether the measurement is complete based on the measurement time from step 122 (129). If not, the repetitive waveform continues to be applied. If complete, the stored sampled data array is analyzed (130) by the procedure shown in FIG. 25, and the measurement is stopped (131). The data shown in FIG. 17 and FIG. 23 were obtained using this approach. In addition to the approaches discussed above, other approaches for obtaining repetitive measurement data are known to those skilled in the art.

Applications

The apparatus of the present invention provides for simultaneous measurement of thickness and group index of refraction. For example, these simultaneous measurements can be made on a solid, a free-falling liquid, a liquid layer moving along a horizontal plane, or a liquid layer flowing down a stationary inclined plane. For the case of a liquid flowing down an inclined plane the dynamic viscosity can also be measured. Physical properties of optically transparent fluids or liquids can be measured since the method functions by measuring distances to optical interfaces and is insensitive to differing optical absorptions. Width-wise thickness uniformity profiles can be obtained by moving the apparatus across the width of a web or sheet material being measured.

Further, the apparatus of the present invention can be used to measure photosensitive liquid layers. For such photosensitive liquid layers, the light source needs to be in a region of the optical spectrum where the photosensitive materials have minimal absorption (e.g. a center of wavelength of 1200 to 1600 nm). Near-infrared LEDs with wavelengths of 1300 nm or 1550 nm, which are standard wavelengths in optical communications, are suitable for these applications.

LEDs of 1300 nm wavelength light are advantageous since communication grade single-mode optical fibers have minimal chromatic dispersion at this wavelength. For materials which are near-infrared sensitive, the light source needs to be in a different region of the optical spectrum.

Figure 27:
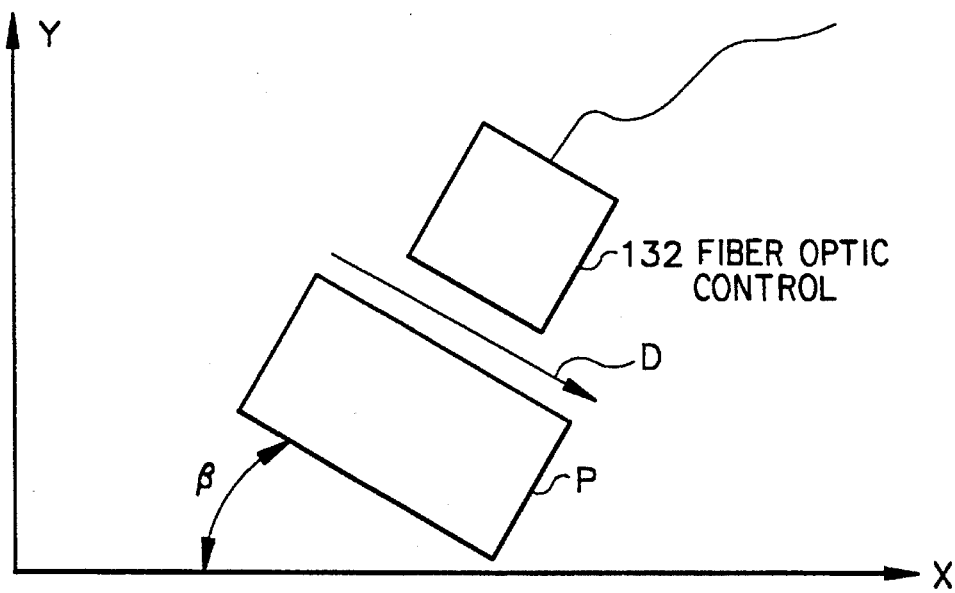
FIG. 27 shows a measurement geometry for a liquid flowing down a stationary inclined plane.

The following discussion relates to a method for measuring viscosity by means of the present invention. FIG. 27 shows a schematic of a stationary inclined plane P over which a liquid can flow in the direction shown by arrow D. Plane P is inclined by an angle $\beta$ with respect to the horizontal axis x. A fiber-optic probe 132 is located above plane P so as to be normal to the surface of plane P.

For a Newtonian fluid, it can be shown that the average thickness of a liquid flowing down inclined plane P is a function of the fluid viscosity $\eta$, density $\rho$, volume flow rate per unit width Q, acceleration of gravity g, and plane angle $\beta$. The average thickness can be calculated from the relationship:

$$t = \left( \frac{3Q\eta}{\rho g \sin\beta} \right)^{1/3} \quad (11)$$

Accordingly, the fluid viscosity $\eta$ of liquid L can be calculated from a knowledge of the other parameters in Equation 11.

The total volumetric flow rate VFR of the liquid is given by:

$$VFR = Qw \quad (12)$$

where w is the width of plane P.

Figure 28:
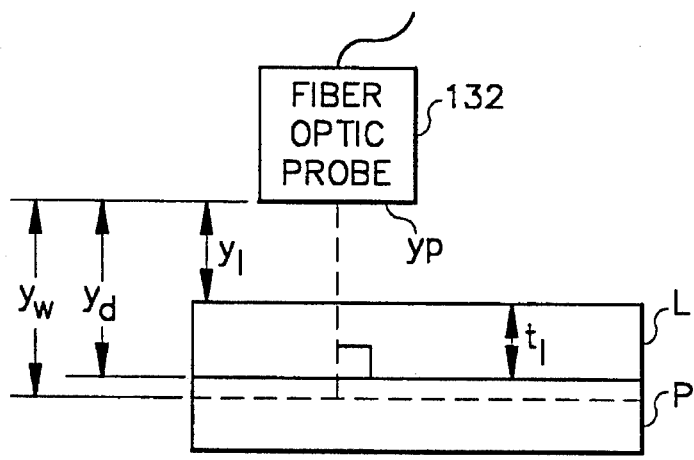
FIG. 28 shows the measurement geometry for measuring the thickness of a liquid on a plane.

FIG. 28 shows the measurement geometry for measuring the thickness of liquid L on non-inclined plane P. The values are measured from the tip $y_p$ of the optical probe 132:

$y_1$=distance to the liquid layer surface;

$y_d$=actual distance to plane P;

$y_w$=apparent distance to plane P when liquid layer is present;

$n_1$=group index of refraction of the liquid;

$t_1$=liquid layer thickness;

OPD=optical path difference.

The corresponding relationships between these values are:

$$t_1 = y_d - y_l \quad (13)$$
$$OPD = n_1 t_1 = y_w - y_l \quad (14)$$

$$n_1 = \frac{y_w - y_l}{y_d - y_l} \quad (15)$$

Figure 29:
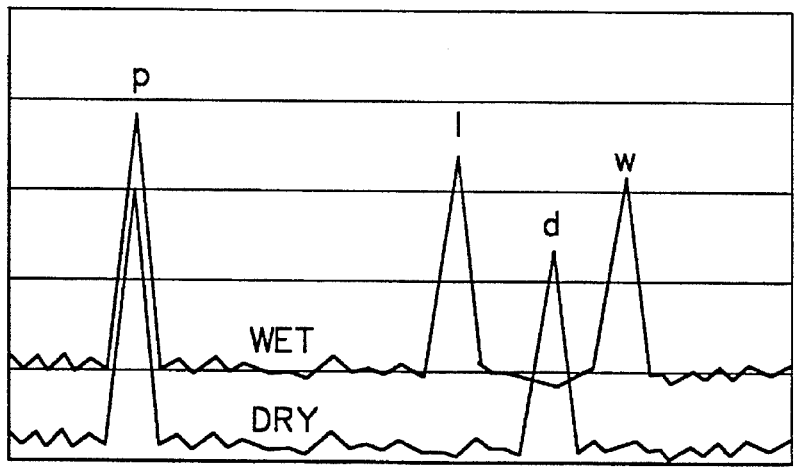
FIG. 29 shows simulated graphs of data with and without liquid present on a plane.

FIG. 29 shows a plot of simulated data obtained with optical probe 132 when the liquid layer is absent (i.e. plane P is DRY), and when the liquid layer is present (i.e., plane P is WET). The intensity of the measured envelope signal is plotted as a function of the optical path difference measured by the interferometers. Analysis of the peak positions allows calculation of the liquid layer thickness and group index of refraction, as follows.

When the liquid layer is absent during a measurement cycle, two peaks are observed for each scan of motor 30. The two peaks are (i) the reflection (p) from the surface of optical probe 132, and (ii) the reflection (d) from the surface of plane P.

When the liquid layer is present, three peaks are observed. As shown in FIG. 29, the leftmost peak (p) is a reflection from the surface of optical probe 132, the center peak (1) is a reflection from the air-liquid interface, and the rightmost peak (w) is a reflection from the liquid-plane P interface. Notice that the apparent location (w) of the plane P reflection shifts to the right when liquid is present. This is a result of the fact that the instrument measures optical path difference, and the group index of refraction of the liquid layer is greater than 1.0, thereby increasing the effective optical path (w) to the surface of plane P.

Figure 30:
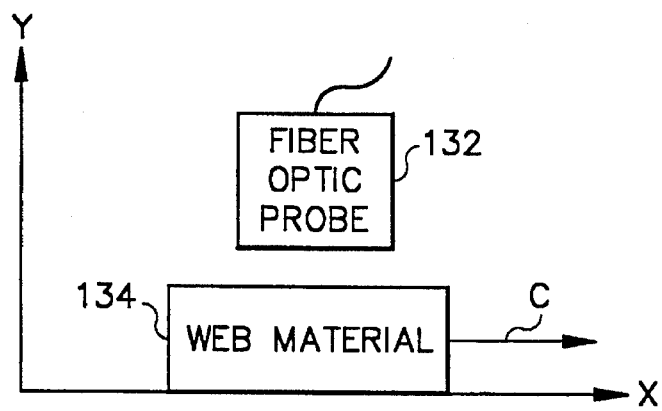
FIG. 30 shows the measurement geometry for measuring the thickness of a moving web.
Figure 31:
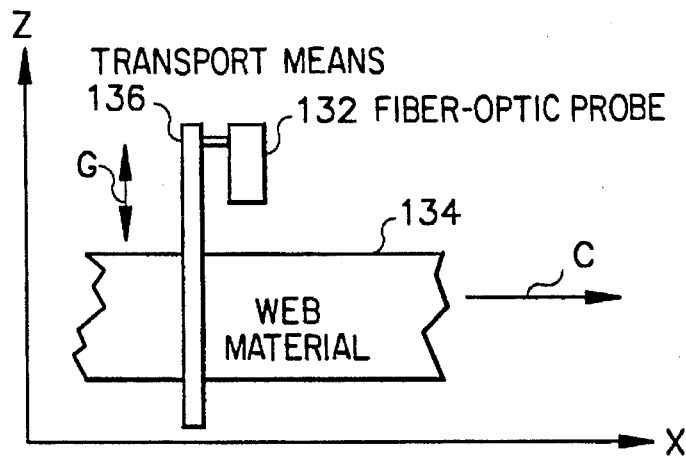
FIG. 31 shows the measurement geometry for measuring widthwise thickness profiles of a moving web.

FIG. 30 shows a schematic of a web material 134 traveling in the direction shown by arrow C. Web material 134 can carry a liquid layer, or other coating. Fiber-optic probe 132 is oriented so as to be normal to the surface of web material 134. To determine the thickness uniformity across the width of a web material, fiber-optic probe 132 can be mounted on a transport means (or traversing frame) 136 to be moved across the width of the web material 134, as shown in FIG. 31, in the direction of arrow G. Surface profiling of extended objects (e.g., webs, sheets) can also be performed using a probe mounted on a transport means as described above. The analysis for a moving web is similar to that described above for a liquid flowing on inclined plane P. However, the volume flow rate per unit width Q is not applicable. Similarly, measurements can also be made on stationary web material or free-falling liquids. Likewise, longitudinal measurements can be made of moving webs with probe 132 being fixedly mounted.

The analysis for multiple layers is a extension of the analysis discussed above for single layer systems. To observe interfaces in multiple layer systems, there must be a group index of refraction difference between the layers. As an example, consider a two layer system with group indices of refraction of $n_1$ and $n_2$, and thicknesses $t_1$ and $t_2$, respectively. The observed distance between the first two reflections will be $n_1 t_1$, while the observed distance between the second and third reflections will be $n_2 t_2$ without an optical probe reflection present. Likewise, for a three layer system, the next observed distance would be $n_3 t_3$. A coextruded web is an example of a multiple layer system which can be analyzed as above.

Figure 32:
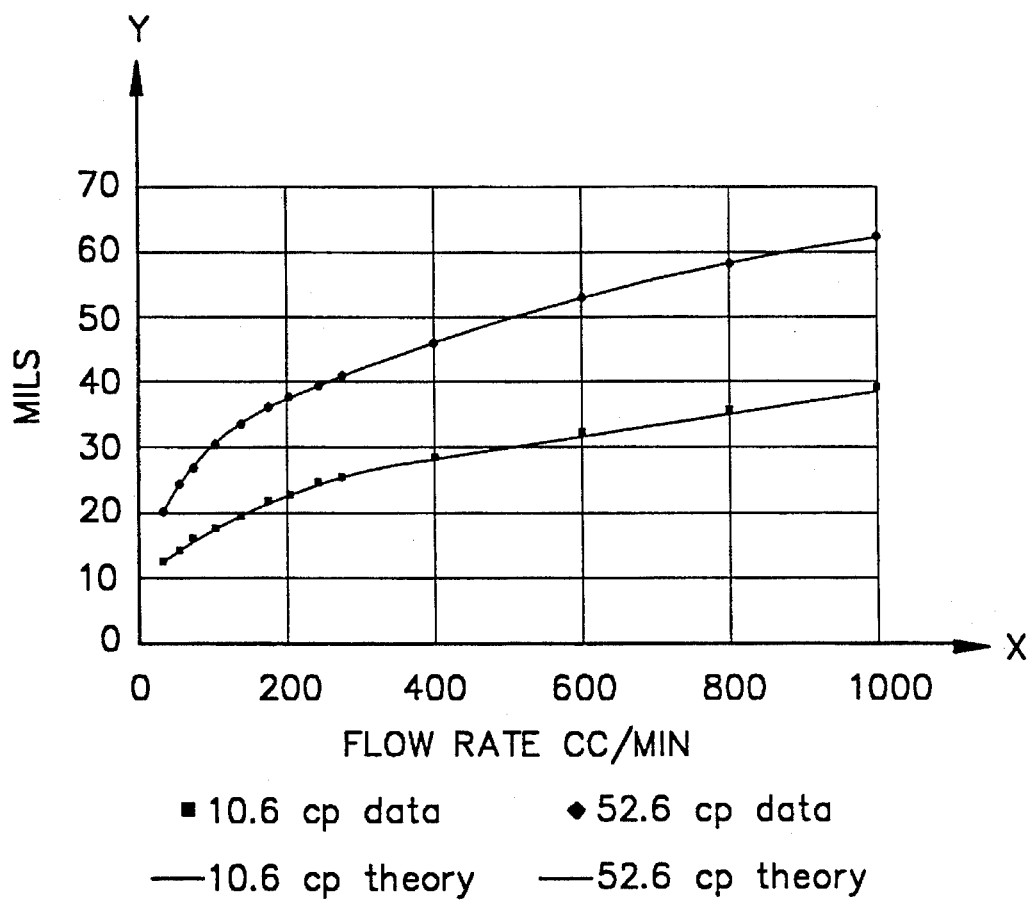
FIG. 32 shows thickness versus flow rate data for glycerin-water mixtures.

The analysis of a liquid flowing down an inclined plane is similar to the analysis described above for measuring the group index of refraction with the back surface of object 25 and the mirror coincident in space. Analyses were performed with liquids flowing down a 6 inch wide inclined plane P. Model Newtonian liquids consisting of glycerin-water mixtures ranging in viscosity from 9 to 53 centipoise (cp) were investigated. Liquid thickness was measured as a function of flow rate over the range of 10–1000 cc/min. The solutions were metered with high accuracy gear pumps. Transparent and dye-containing solutions were evaluated, and no significant differences were observed between the two types of solutions. The measured thickness versus flow rate was compared to theoretical expressions based on Newtonian flow equations. Measurements were made with both the standard mode apparatus and the autocorrelation mode apparatus. Measured thicknesses were within 1% of the theoretical values in all cases. FIG. 32 shows plots of measured and theoretical thicknesses for glycerin-water mixtures with two different viscosities.

The thickness versus flow rate data for the Newtonian liquids were utilized to calculate the viscosity of the solutions. Table 2 summarizes these calculations. Also listed are the viscosities measured with a Haake viscometer. The standard deviation of the data show high precision for this type of measurement, and the $\Delta\%$ column shows the relative differences between the Haake viscometer and the standard mode apparatus measured viscosity values. The calculated results compare favorably with the Haake viscometer data. Differences can be accounted for by temperature variations in the laboratory since there is a strong temperature dependence on the viscosity of glycerin.

TABLE 2

CALCULATED VERSUS MEASURED VISCOSITY DATA

| Haake cp | calc. cp. | σ | Δ % | Δ σ |
|---|---|---|---|---|
| 10.6 | 10.81 | 0.616 | 1.98 | 0.34 |
| 52.6 | 51.98 | 1.020 | −1.18 | −0.61 |
| 51.4 | 50.83 | 0.787 | −1.19 | −0.78 |
| 11.7 | 11.82 | 0.401 | 0.60 | 0.17 |
| 9.38 | 9.26 | 0.157 | −1.28 | −0.76 |
| 30.7 | 29.33 | 0.640 | −4.49 | −2.16 |
| 50.3 | 48.10 | 0.954 | −4.34 | −2.29 |
| 9.38 | 9.36 | 0.145 | −0.21 | −0.14 |

Figure 33:
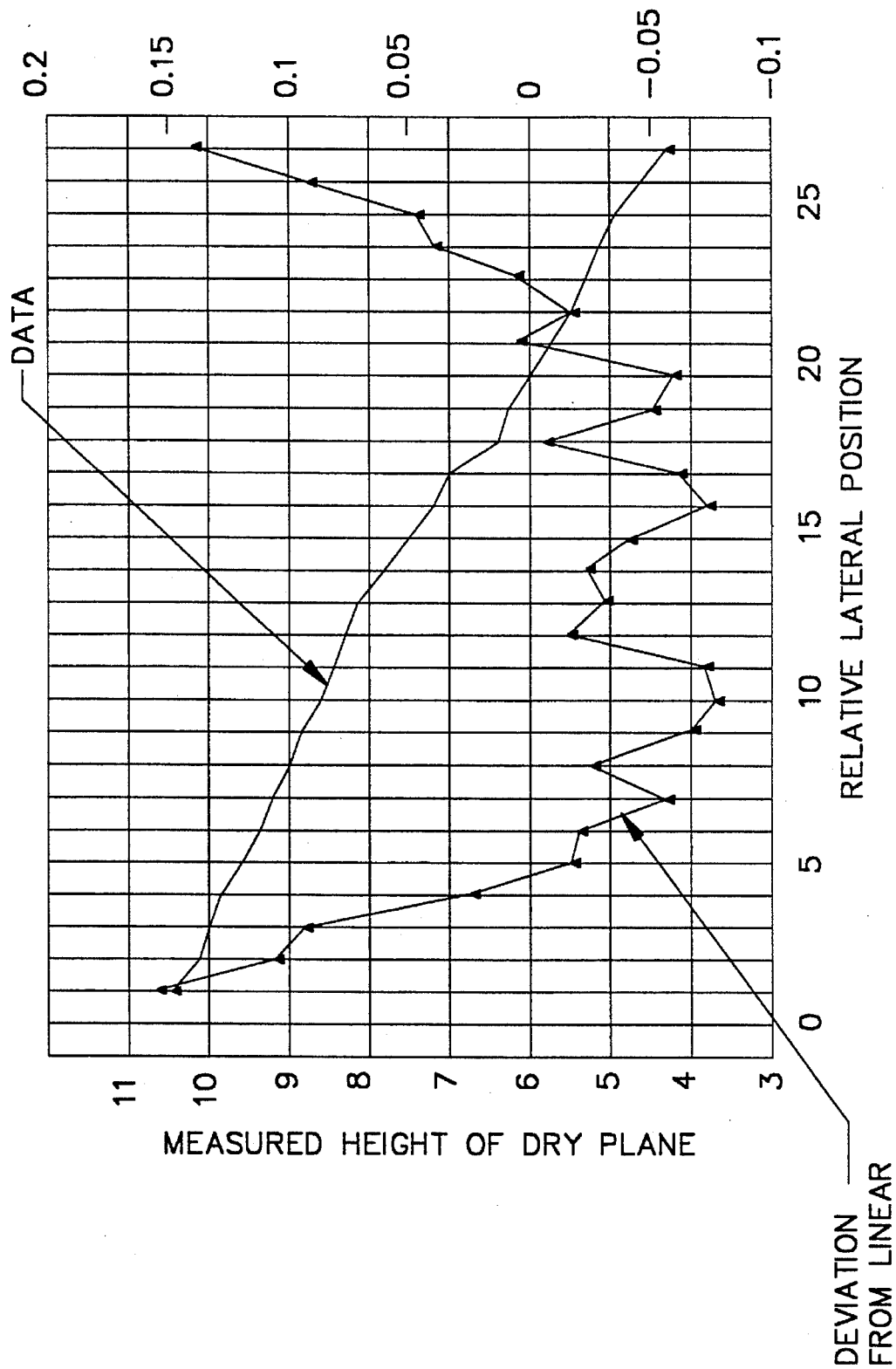
FIG. 33 shows distance to an inclined plane data as a function of relative lateral position.

An example of surface profiling of an extended object is now described. Analyses were performed utilizing an extended inclined plane (as object 25) to determine widthwise sag of the inclined plane. For these analyses, optical probe 132 was mounted on traversing frame 136 approximately 10 mm above the surface of the inclined plane. The probe tip $x_p$ of optical probe 132 has a stationary reflective surface, the reflective surface facing object 25. Traversing frame 136 and the inclined plane were not exactly parallel. Distance from the probe tip $y_p$ to the surface of the inclined plane was continuously measured at a measurement rate of 10 Hz while traversing frame 136 was traversing at a rate of 1 inch/sec. These data are shown in FIG. 33 along with a linear regression analysis fit to the data. The deviations from a linear fit (indicative of deviation flatness of the surface of the object) are plotted and are indicated on the axis to the right of the plot. The relative angle between the translation stage and the inclined plane was calculated to be 0.135 degrees from the linear regression analysis. The data also indicate that the inclined plane sags in the center as shown by the deviations from the linear data fit.

An apparatus has been described in which a coherent light interferometer is utilized to provide data acquisition trigger signals at constant distance intervals for sampling of non-coherent light interferometer data. Velocity control of the motor is not needed during the measurement cycle. There is also no need for a home reference position. Further, once the apparatus is initially set up and calibrated, there is no need for further calibration in the field. In addition, the non-coherent light interferometer may include a plurality of non-coherent light sources operating at different wavelengths. This allows for simultaneous measurement of more than one physical property of the object, such as group index of refraction and thickness.

Figure 34:
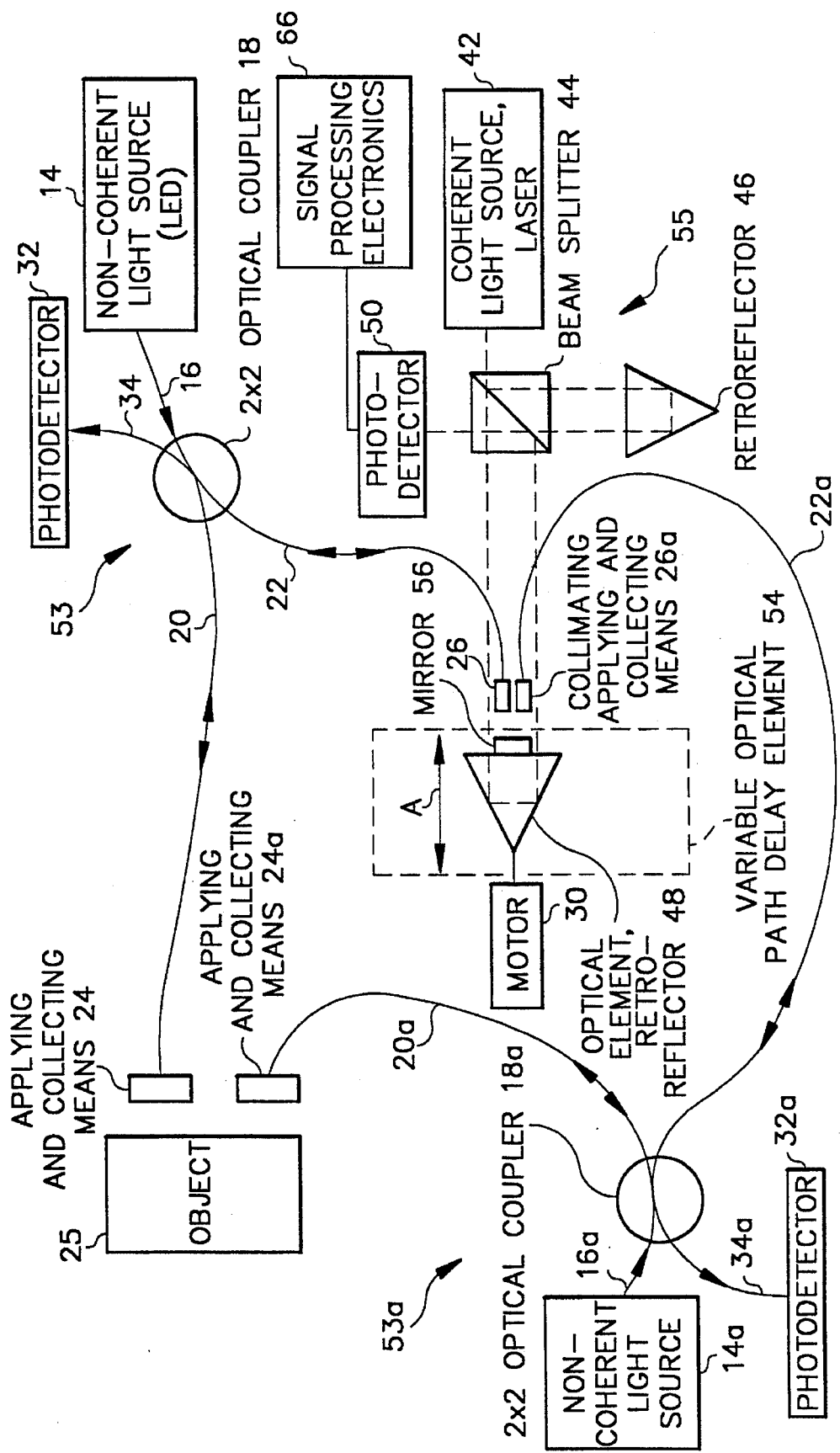
FIG. 34 shows a multiplexed measurement apparatus of the present invention having two non-coherent light interferometers.

Other alternative embodiments include multiple non-coherent light interferometers which share common variable optical path delay element 54. Such embodiments are useful in optical multiplexing applications, and allow simultaneous monitoring of multiple locations of object 25, simultaneous monitoring of multiple objects with a single measurement apparatus, or simultaneously monitoring of more than one physical property of object 25. For example, FIG. 34 illustrates such an embodiment having two non-coherent light interferometers 53, 53a. Noncoherent light interferometer 53a includes LED 14a, applying and collecting means 24a, collimating applying and collecting means 26a, photodetector 32a, optical coupler 18a, and optical fibers 16a, 20a, 22a, 34a. As shown in FIG. 34, applying and collecting means 24, 24a are incident on object 25, at different locations. Alternatively, applying and collecting means 24, 24a can be incident on different objects. Additional non-coherent light interferometers can be added in a similar manner. Optionally, light source 14, 14a can be the same light source by addition of a 1×2 optical coupler (not shown). Such multiplexing configurations also apply to optical autocorrelation mode apparatus 72 shown in FIG. 20. Multiplexed configurations consisting of combinations of standard mode apparatus 52 and autocorrelation mode apparatus 72 are possible.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

Parts List 10 prior art, fiber-optic embodiment of a non-coherent light interferometer
14 non-coherent light source
16 optical fiber
18 2×2 optical coupler
20 optical fiber
22 optical fiber
24 applying and collecting means
25 object
26 collimating applying and collecting means
28 optical element; retroreflector, mirror, or a combination of the two
30 actuation means; motor
32 photodetector
34 optical fiber
40 coherent light interferometer
42 coherent light source; laser
44 beam splitter
46 retroreflector
48 optical element; retroreflector
50 photodetector
52 dual interferometer apparatus; standard mode
53 non-coherent light interferometer of the invention
54 common variable optical path delay element
55 coherent light interferometer of the invention; laser interferometer
56 optical element; mirror
58 mounting mean
60 motor drive control electronic module
62 electronic module
64 computer system
66 signal processing electronics
68 normal cleaved fiber probe
70 mirror
72 optical autocorrelation mode apparatus
73 optical fiber
74 2×1 single-mode optical coupler
75 single-mode optical fiber
76 stationary reference reflector
78 collimating applying and collecting means
80–100 flowchart steps
110–116 flowchart steps
120–131 flowchart steps
132 fiber-optic probe
134 web material
136 transport means; traversing frame

What is claimed is:

1. A method for determining a physical property of an object having at least one surface which reflects light, said method comprising the steps of:

providing a first and second interferometer in association by means of sharing a common variable optical path delay element, said first interferometer having a coherent light source having a wavelength $\lambda_c$ and forming a coherent light interference signal, said second interferometer having a non-coherent light source;

positioning the object such that said non-coherent light source is incident the object;

forming a non-coherent light interference signal indicative of the physical property of the object;

displacing said variable optical path delay element with a periodic, continuously-varying velocity profile and measuring said coherent light interference signal as a function of displacement of said variable optical path delay element, the displacement of said variable optical path delay element being over a distance sufficient to determine the physical property of the object;

utilizing said coherent light interference signal to generate data acquisition trigger signals at constant displacement intervals of said variable optical path delay element;

utilizing said generated data acquisition trigger signals to sample the amplitude of said non-coherent light interference signal; and determining the physical property of the object from said non-coherent light interference signal.

2. A method according to claim 1 further comprising the step of positioning the object in a light source branch of said second interferometer.

3. A method according to claim 1 further comprising the step of positioning the object in an interfering branch of said second interferometer.

4. A method according to claim 1 wherein the step of displacing said variable optical path delay element, alternately monotonically increases and monotonically decreases the optical path delay of said variable optical path delay element over said distance sufficient to determine the physical property of the object.

5. A method according to claim 1 wherein said data acquisition trigger signals are generated at constant displacement intervals equal to $\lambda_c/4$ of said variable optical path delay element, and the step of utilizing said data acquisition trigger signals utilizes a subset of said data acquisition trigger signals at constant displacement intervals equal to $n\lambda_c/4$ to sample the amplitude of said non-coherent light interference signal at said constant displacement intervals, n being a small integer selected such that less than two points per fringe frequency of the non-coherent light source are sampled.

6. A method according to claim 1 wherein said second interferometer further comprises an optical probe tip having a stationary reflective surface, and said method further comprises the steps of:

mounting said optical probe to a traversing frame such that the reflective surface faces the object; and traversing the optical probe across the object.

7. A method for determining a physical property of an object having at least one surface which reflects light, said method comprising the steps of:

providing a coherent light source emitting a coherent light signal;

dividing said coherent light signal into first and second light signals;

applying said first light signal to a stationary reference device, a portion of said first light signal being reflected by said stationary reference device to form a reference signal;

applying said second light signal to a variable optical path delay element to form a first delay signal;

collecting said reference signal;

providing a non-coherent light source emitting a non-coherent light signal;

positioning the object such that said non-coherent light source is incident the object;

dividing said non-coherent light signal into third and fourth light signals;

applying a portion of said third light signal to the object, a portion of said third light signal being reflected by the object to form an object signal indicative of the physical property of the object;

collecting said object signal;

applying said fourth light signal to said variable optical path delay element to form a second delay signal;

collecting said first delay signal;

collecting said second delay signal;

displacing said variable optical path delay element with a periodic, continuously-varying velocity profile to vary the optical path length of said second light signal and said fourth light signal as a function of displacement of said variable optical path delay element, said variable optical path delay element being movable over a distance sufficient to determine the physical property of the object;

combining said first delay signal and said reference signal to form a coherent light interference signal;

combining said object signal and said second delay signal to form a non-coherent light interference signal;

measuring said coherent light interference signal as a function of displacement of said variable optical path delay element;

generating data acquisition trigger signals at constant displacement intervals of said variable optical path delay element based on said coherent light interference signal;

utilizing said data acquisition trigger signals to sample the amplitude of said non-coherent light interference signal; and determining the physical property of the object from said amplitude.

8. A method according to claim 7 wherein the coherent light source has a wavelength $\lambda_c$, said data acquisition trigger signals are generated at constant displacement intervals equal to $\lambda_c/4$ of said variable optical path delay element, and the step of utilizing said data acquisition trigger signals utilizes a subset of said data acquisition trigger signals at constant displacement intervals equal to $n\lambda_c/4$ to sample the amplitude of said non-coherent light interference signal at said constant displacement intervals, n being a small integer selected such that less than two points per fringe frequency of the non-coherent light source are sampled.

9. A method for determining a physical property of an object having at least one surface which reflects light, said method comprising the steps of:

providing a coherent light source emitting a coherent light signal;

dividing said coherent light signal into first and second light signals;

applying said first light signal to a first stationary reference device, a portion of said first light signal being reflected by said first stationary reference device to form a first reference signal;

collecting said first reference signal;

providing a non-coherent light source emitting a non-coherent light signal;

positioning the object such that said non-coherent light source is incident the object;

applying a portion of said non-coherent light signal to the object, a portion of said non-coherent light signal being reflected by said object to form an object signal indicative of the physical property of the object;

collecting said object signal;

dividing said object signal into third and fourth light signals;

applying said third light signal to a second stationary reference device, a portion of said third light signal being reflected by said second stationary reference device to form a second reference signal;

collecting said second reference signal;

applying said second light signal to a variable optical path delay element to form a first delay signal;

applying said fourth light signal to said variable optical path delay element to form a second delay signal, said variable optical path delay element varying the optical path length of said second light signal and said fourth light signal;

collecting said first delay signal;

collecting said second delay signal;

displacing said variable optical path delay element with a periodic, continuously-varying velocity profile to vary the optical path length of said second light signal and said fourth light signal as a function of displacement of said variable optical path delay element, said variable optical path delay element being movable over a distance sufficient to determine the physical property of the object;

combining said first delay signal and said first reference signal to form a coherent light interference signal;

combining said second delay signal and said second reference signal to form a non-coherent light interference signal;

measuring said coherent light interference signal as a function of displacement of said variable optical path delay element;

generating data acquisition trigger signals at constant displacement intervals of said variable optical path delay element based on said coherent light interference signal;

utilizing said data acquisition trigger signals to sample the amplitude of said non-coherent light interference signal; and determining the physical property of the object from said amplitude.

10. A method according to claim 9 wherein the coherent light source has a wavelength $\lambda_c$, said data acquisition trigger signals are generated at constant displacement intervals equal to $\lambda_c/4$ of said variable optical path delay element, and the step of utilizing said data acquisition trigger signals utilizes a subset of said data acquisition trigger signals at constant displacement intervals equal to $n\lambda_c/4$ to sample the amplitude of said non-coherent light interference signal at said constant displacement intervals, n being a small integer selected such that less than two points per fringe frequency of the non-coherent light source are sampled.

11. A method for determining the physical properties of an object having at least one surface which reflects light, said method comprising the steps of:

providing a first interferometer having a coherent light source and forming a coherent light interference signal;

providing a second interferometer having a non-coherent light source incident the object and forming a non-coherent light interference signal indicative of the physical property of the object, said first and second interferometers being in association so as to share a common variable optical path delay element;

activating said coherent and non-coherent light interferometers;

displacing said common variable optical path delay element in a first direction with a periodic, continuously-varying velocity profile;

generating data acquisition trigger signals from said coherent light interference signal;

sampling said non-coherent light interference signal utilizing said data acquisition trigger signals;

digitizing said sampled non-coherent light interference signal;

storing said digitized, sampled non-coherent light interference signal in a data array;

displacing said common variable optical path delay element in a second direction with a periodic, continuously-varying velocity profile, said second direction being different than said first direction;

generating data acquisition trigger signals from said coherent light interference signal;

sampling said non-coherent light interference signal utilizing said data acquisition trigger signals;

digitizing said sampled non-coherent light interference signal;

storing said digitized, sampled non-coherent light interference signal in a data array; and analyzing said stored data array to determine the physical property of the object.

12. A method according to claim 9 wherein said step of analyzing said stored data array comprises the steps of:

calculating an absolute value array of said data array;

performing a Gaussian weighted average of said absolute value array;

locating a Gaussian maxima;

performing a regression analysis; and calculating the physical property of the object.

13. A method according to claim 11 wherein the coherent light source has a wavelength $\lambda_c$, said data acquisition trigger signals are generated at constant displacement intervals equal to $\lambda_c/4$ of said variable optical path delay element, and the step of utilizing said data acquisition trigger signals utilizes a subset of said data acquisition trigger signals at constant displacement intervals equal to $n\lambda_c/4$ to sample the amplitude of said non-coherent light interference signal at said constant displacement intervals, n being a small integer selected such that less than two points per fringe frequency of the non-coherent light source are sampled.

14. A method for determining the physical property of an object having at least one surface which reflects light, said method comprising the steps of:

providing a first interferometer having a coherent light source having a wavelength $\lambda_c$ and forming a coherent light interference signal;

providing a second interferometer having a non-coherent light source incident the object and forming a non-coherent light interference signal indicative of the physical property of the object, said first and second interferometers being in association so as to share a common variable optical path delay element;

determining a measurement rate;

determining a measurement time;

monitoring said coherent light interference signal and said non-coherent light interference signal;

displacing said variable optical path delay element with a periodic, continuously-varying velocity profile;

generating data acquisition trigger signals at constant displacement intervals equal to $\lambda_c/4$ of said variable optical path delay element from said coherent light interference signal;

sampling said non-coherent light interference signal utilizing a subset of said data acquisition trigger signals at constant displacement intervals equal to $\lambda_c/4$ to sample the amplitude of said non-coherent light interference signal at said constant displacement intervals, n being a small integer selected such that less than two points per fringe frequency of the non-coherent light source are sampled;

digitizing said sampled non-coherent light interference signal;

storing said digitized, sampled non-coherent light interference signal in a data array; and analyzing said stored data array.

15. A method according to claim 14 wherein said step of analyzing said stored data array comprises the steps of:

calculating an absolute value array of said data array;

performing a Gaussian weighted average of said absolute value array;

locating a Gaussian maxima;

performing a regression analysis; and calculating the physical property of the object.

16. A method for determining multiple physical properties of an object having at least one surface which reflects light, said method comprising the steps of:

providing a first, second, and third interferometer in association by means of sharing a common variable optical path delay element, said first interferometer having a coherent light source and forming a coherent light interference signal, each of said second and third interferometers having a non-coherent light source incident the object and forming a non-coherent light interference signal indicative of a physical property of the object;

displacing said variable optical path delay element with a periodic, continuously-varying velocity profile and measuring the amplitude of said coherent light interference signal as a function of displacement of said variable optical path delay element, the displacement of said variable optical path delay element being over a distance sufficient to determine the physical property of the object;

utilizing said coherent light interference signal to generate data acquisition trigger signals at constant displacement intervals of said variable optical path delay element;

measuring the amplitude of each of said non-coherent light interference signals;

utilizing said generated data acquisition trigger signals to sample the amplitude of each of said non-coherent light interference signals; and determining a physical property of the object from each of said sampled non-coherent light interference signals.

17. A method according to claim 16 wherein the coherent light source has a wavelength $\lambda_c$, said data acquisition trigger signals are generated at constant displacement intervals equal to $\lambda_c/4$ of said variable optical path delay element, and the step of utilizing said data acquisition trigger signals utilizes a subset of said data acquisition trigger signals at constant displacement intervals equal to $n\lambda_c/4$ to sample the amplitude of said non-coherent light interference signal at said constant displacement intervals, n being a small integer selected such that less than two points per fringe frequency of the non-coherent light source are sampled.

18. A method for simultaneously determining a physical property of a plurality of objects having at least one surface which reflects light, said method comprising the steps of:

providing a coherent light interferometer having a coherent light source and forming a coherent light interference signal;

providing a plurality of non-coherent light interferometers, each of said plurality of non-coherent light interferometers having a non-coherent light source incident the respective object and forming a non-coherent light interference signal indicative of a physical property of each of said respective plurality of objects, said coherent light interferometer and said plurality of non-coherent light interferometers in association by means of sharing a common variable optical path delay element;

displacing said variable optical path delay element with a periodic, continuously-varying velocity profile and measuring the amplitude of said coherent light interference signal as a function of displacement of said variable optical path delay element, the displacement of said variable optical path delay element being over a distance sufficient to determine the physical property of the object;

utilizing said coherent light interference signal to generate data acquisition trigger signals at constant displacement intervals of said variable optical path delay element;

measuring the amplitude of each of said non-coherent light interference signals;

utilizing said generated data acquisition trigger signals to sample the amplitude of each of said non-coherent light interference signals; and determining a physical property of each of said respective plurality of objects from each of said respective sampled non-coherent light interference signals.

19. A method according to claim 18 wherein the coherent light source has a wavelength $\lambda_c$, said data acquisition trigger signals are generated at constant displacement intervals equal to $\lambda_c/4$ of said variable optical path delay element, and the step of utilizing said data acquisition trigger signals utilizes a subset of said data acquisition trigger signals at constant displacement intervals equal to $n\lambda_c/4$ to sample the amplitude of said non-coherent light interference signal at said constant displacement intervals, n being a small integer selected such that less than two points per fringe frequency of the non-coherent light source are sampled.

* * * * *